US012564313B2

(12) United States Patent
Walters et al.

(10) Patent No.: US 12,564,313 B2
(45) Date of Patent: *Mar. 3, 2026

(54) SYSTEMS AND METHODS OF INTEGRATED REAL-TIME VISUALIZATION

(71) Applicant: INTUITIVE SURGICAL OPERATIONS, INC., Sunnyvale, CA (US)

(72) Inventors: Worth B. Walters, Campbell, CA (US); Randall L Schlesinger, San Mateo, CA (US); Oliver J. Wagner, Mountain View, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 534 days.

This patent is subject to a terminal disclaimer.

(21) Appl. No.: 17/667,090

(22) Filed: Feb. 8, 2022

(65) Prior Publication Data

US 2022/0151600 A1     May 19, 2022

Related U.S. Application Data

(63) Continuation of application No. 16/310,383, filed as application No. PCT/US2017/037277 on Jun. 13, 2017, now Pat. No. 11,266,387.

(Continued)

(51) Int. Cl.
*A61B 1/005* (2006.01)
*A61B 1/01* (2006.01)
(Continued)

(52) U.S. Cl.
CPC .............. *A61B 1/005* (2013.01); *A61B 1/009* (2022.02); *A61B 1/01* (2013.01); *A61B 1/05* (2013.01);
(Continued)

(58) Field of Classification Search
CPC ........... A61B 1/005; A61B 1/009; A61B 1/01; A61B 1/05; A61B 1/07; A61B 1/273;
(Continued)

(56) References Cited

U.S. PATENT DOCUMENTS 5,906,579 A     5/1999  Vander et al.
6,527,761 B1 *  3/2003  Soltesz .............. A61B 17/1219
                                                      604/509

(Continued)

FOREIGN PATENT DOCUMENTS

WO     WO-2011028181 A1     3/2011
WO     WO-2015153931 A1     10/2015

OTHER PUBLICATIONS

International Search Report and Written Opinion for Application No. PCT/US2017/037277, mailed on Sep. 14, 2017, 14 pages.

(Continued)

*Primary Examiner* — Jonathan Cwern
(74) *Attorney, Agent, or Firm* — Haynes & Boone, LLP.

(57) ABSTRACT

A method for performing a minimally invasive procedure includes activating a sealing device of a flexible catheter to seal anatomic passageways. The flexible catheter comprises a plurality of first lumens to receive a working catheter and an imaging probe. The method includes determining a position of a distal portion of the flexible catheter, the imaging probe, or the working catheter while the imaging probe is within a first of the plurality of first lumens, the working catheter is within a second of the plurality of first lumens, and the imaging probe and the working catheter extend through the sealing device. The method includes collapsing a portion of the passageways using a third of the plurality of first lumens, one or more second lumens in the working catheter, or one or more third lumens in the imaging probe and capturing an image in the collapsed portion.

16 Claims, 13 Drawing Sheets

Related U.S. Application Data

(60) Provisional application No. 62/350,455, filed on Jun. 15, 2016.

(51) Int. Cl.

| | |
|---|---|
| *A61B 1/05* | (2006.01) |
| *A61B 1/07* | (2006.01) |
| *A61B 1/273* | (2006.01) |
| *A61B 8/00* | (2006.01) |
| *A61B 8/12* | (2006.01) |
| *A61B 17/00* | (2006.01) |
| *A61B 17/34* | (2006.01) |
| *A61B 34/20* | (2016.01) |
| *A61B 90/00* | (2016.01) |

(52) U.S. Cl.
CPC ................ *A61B 1/07* (2013.01); *A61B 1/273* (2013.01); *A61B 8/12* (2013.01); *A61B 8/445* (2013.01); *A61B 17/00234* (2013.01); *A61B 34/20* (2016.02); *A61B 8/4254* (2013.01); *A61B 2017/00296* (2013.01); *A61B 2017/00561* (2013.01); *A61B 2017/3486* (2013.01); *A61B 2034/2051* (2016.02); *A61B 2034/2061* (2016.02); *A61B 2090/3784* (2016.02)

(58) Field of Classification Search
CPC ..... A61B 8/12; A61B 8/445; A61B 17/00234; A61B 34/20; A61B 8/4254; A61B 2017/00296; A61B 2017/00561; A61B 2017/3486; A61B 2034/2051; A61B 2034/2061; A61B 2090/3784; A61B 1/018; A61B 5/065; A61B 5/721; A61M 25/00

See application file for complete search history.

(56) References Cited

U.S. PATENT DOCUMENTS

| | | | |
|---|---|---|---|
| 8,257,303 | B2 | 9/2012 | Moll et al. |
| 11,266,387 | B2* | 3/2022 | Walters ............ A61B 17/00234 |
| 2009/0054761 | A1 | 2/2009 | Voegele et al. |
| 2010/0016757 | A1 | 1/2010 | Greenburg et al. |
| 2012/0289772 | A1 | 11/2012 | O'Connell et al. |
| 2013/0090528 | A1 | 4/2013 | Ramamurthy et al. |
| 2013/0281844 | A1 | 10/2013 | Karino et al. |
| 2013/0317339 | A1 | 11/2013 | Waldstreicher et al. |
| 2014/0343348 | A1* | 11/2014 | Kaplan ................. A61M 5/158 604/21 |
| 2015/0297299 | A1 | 10/2015 | Yeung et al. |
| 2019/0254649 | A1 | 8/2019 | Walters et al. |

OTHER PUBLICATIONS

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

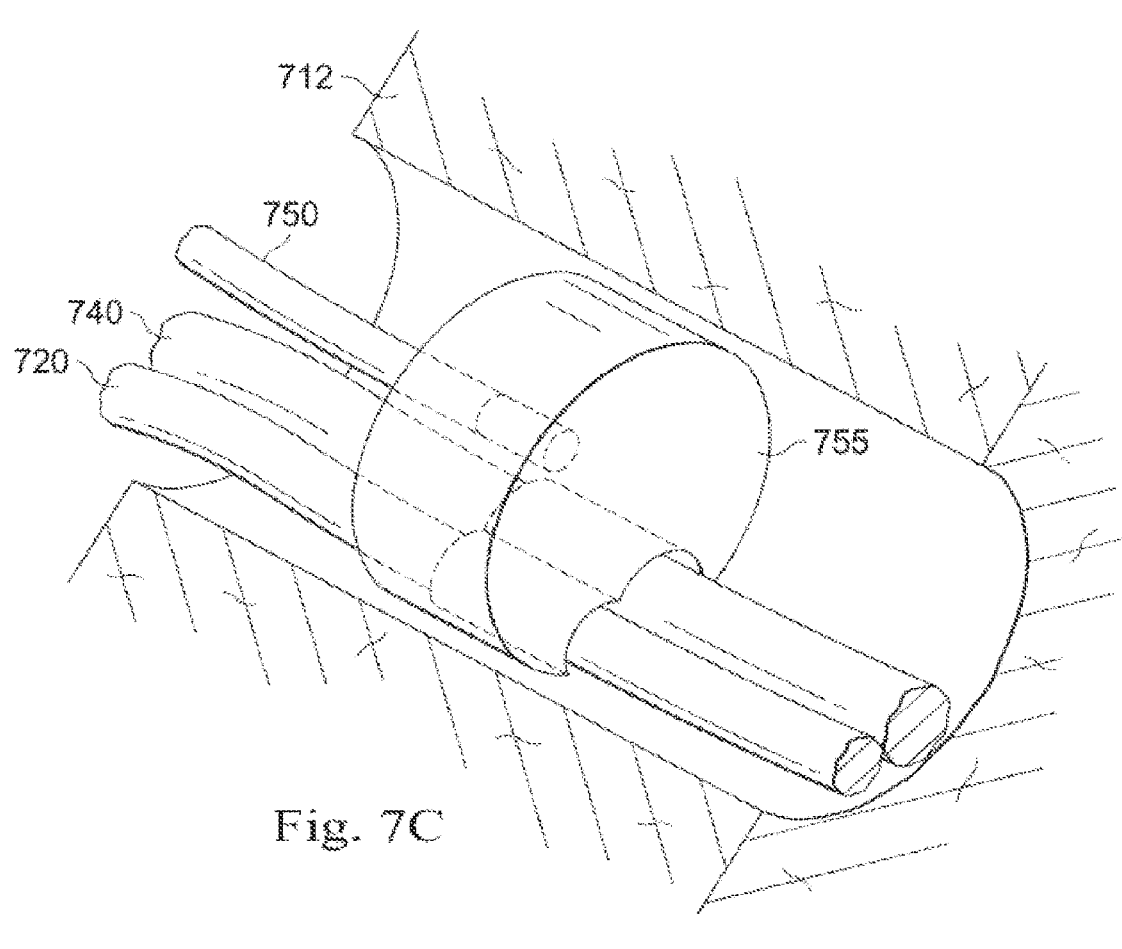
Fig. 7C
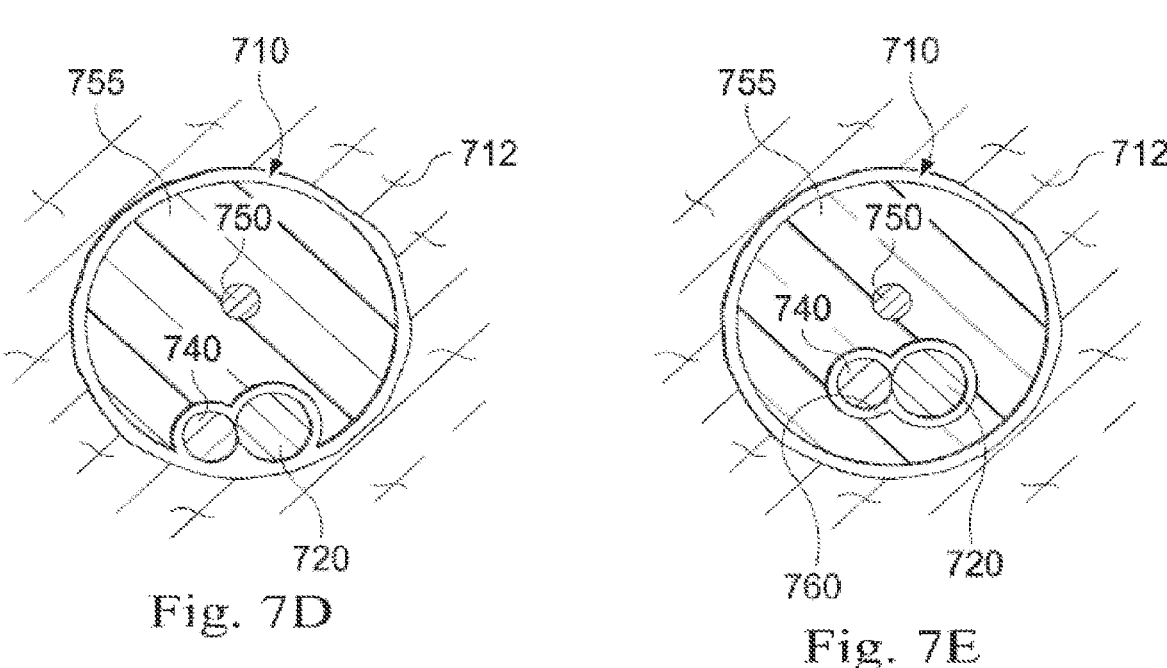
Fig. 7D
Fig. 7E

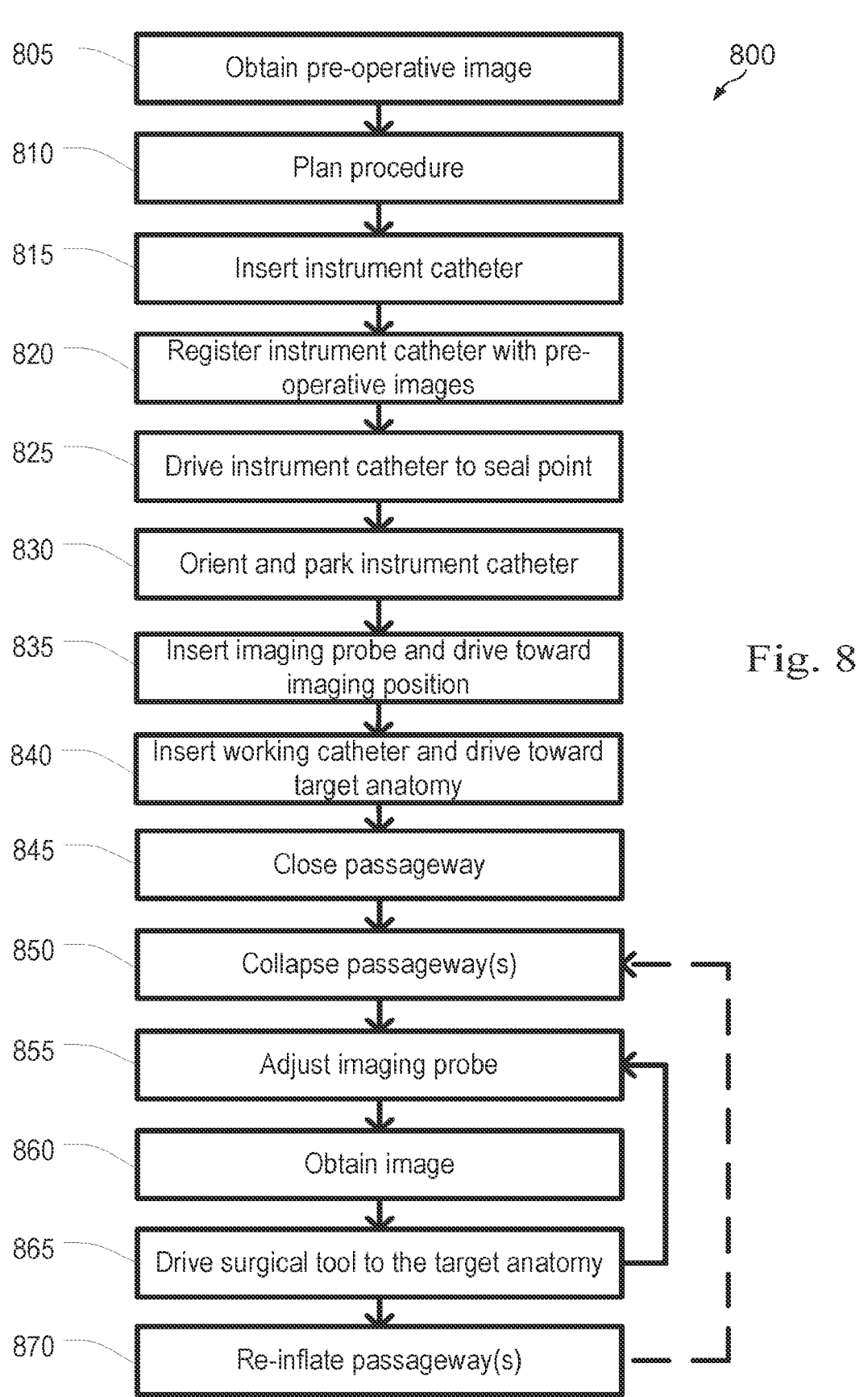

805 — Obtain pre-operative image

800

810 — Plan procedure

815 — Insert instrument catheter

820 — Register instrument catheter with pre-operative images

825 — Drive instrument catheter to seal point

830 — Orient and park instrument catheter

835 — Insert imaging probe and drive toward imaging position

Fig. 8

840 — Insert working catheter and drive toward target anatomy

845 — Close passageway

850 — Collapse passageway(s)

855 — Adjust imaging probe

860 — Obtain image

865 — Drive surgical tool to the target anatomy

870 — Re-inflate passageway(s)

SYSTEMS AND METHODS OF INTEGRATED REAL-TIME VISUALIZATION

CROSS-REFERENCE TO RELATED APPLICATIONS

This patent application is a continuation of U.S. patent application Ser. No. 16/310,383 filed Dec. 14, 2018, which is a U.S. National Stage patent application of International Application No. PCT/US2017/37277 filed Jun. 13, 2017, the benefit which is claimed, and claims priority to and the benefit of the filing date of U.S. Provisional Patent Application No. 62/350,455 entitled "Systems and Methods of Integrated Real-Time Visualization," filed Jun. 15 2016, each of which are incorporated by reference herein in their entireties.

FIELD

The present disclosure is directed to systems and methods for performing minimally invasive procedures using integrated real-time visualization.

BACKGROUND

Minimally invasive medical techniques are intended to reduce the amount of tissue that is damaged during medical procedures, thereby reducing patient recovery time, discomfort, and harmful side effects. Such minimally invasive techniques may be performed through natural orifices in a patient anatomy or through one or more surgical incisions. Through these natural orifices or incisions clinicians may insert minimally invasive medical instruments (including surgical, diagnostic, therapeutic, or biopsy instruments) to reach a target tissue location. One such minimally invasive technique is to use a flexible and/or steerable catheter that is inserted into anatomic passageways and navigated toward a region of interest within the patient anatomy. A minimally invasive medical device, due to its generally small size, does not always provide a surgeon, clinician, or operator or other medical personnel with sufficient imaging capabilities to identify the target tissue location, such as when the target tissue location is located below a surface of a passageway through which the minimally invasive medical device is introduced.

Accordingly, it would be advantageous to provide integrated real-time visualization to aid a surgeon during minimally invasive medical techniques.

SUMMARY

The embodiments of the invention are best summarized by the claims that follow the description.

Consistent with some embodiments, a medical system for performing a minimally invasive procedure within anatomic passageways includes a flexible catheter including a plurality of first lumens and a sealing device, an imaging probe including one or more imaging elements wherein the imaging probe is configured to be slideably received within a first of the plurality of first lumens; a working catheter configured to be slideably received within a second of the plurality of first lumens, and a positioning system configured to determine a position of at least one of a distal portion of the flexible catheter, a distal portion of the imaging probe, and a distal portion of the working catheter within the anatomic passageways. In some embodiments, the sealing device includes a plurality of second lumens and the flexible catheter and the imaging probe are each optionally deployed through a respective one of the second lumens. In some embodiments, the one or more imaging elements include one or more ultrasound transducers. In some embodiments, the sealing device seals the anatomic passageways at a sealing location using one or more balloons, and the anatomic passageways distal to the sealing location are collapsed.

Consistent with some embodiments, a method of planning a medical procedure on target anatomy includes receiving an anatomical model comprising a model of anatomic passageways, determining a target anatomy within the anatomic passageways; determining a first location to position a distal portion of a working catheter where one or more medical instruments deployed through one or more lumens of the working catheter have access to the target anatomy, determining a second location within the anatomic passageways to position a distal portion of an imaging probe where one or more imaging elements of the imaging probe are able to obtain images of the target anatomy, and determining a third location within the anatomic passageways to position a distal portion of a flexible catheter wherein the third location is proximal to the first location and to the second location.

Consistent with some embodiments, a medical system for performing a minimally invasive procedure within anatomic passageways includes a working catheter comprising one or more first lumens, an imaging probe comprising one or more imaging elements positioned near a distal portion of the imaging probe to obtain images of a target anatomy, a flexible catheter comprising a sealing device; and a first positioning system for determining a position of a distal portion of the working catheter, a position of the distal portion of the imaging probe, and a position of a distal portion of the flexible catheter within the anatomic passageways.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

FIG. 7C is a simplified diagram of a cut-away view of the medical instruments and patient anatomy of FIG. 7B according to some additional embodiments.

FIGS. 7D and 7E are simplified diagrams of cross-sectional views of the medical instruments and patient anatomy of FIG. 7B according to some additional embodiments.

FIG. 8 is a simplified diagram of a method of performing a procedure using integrated real-time imaging according to some embodiments.

Figure 1:
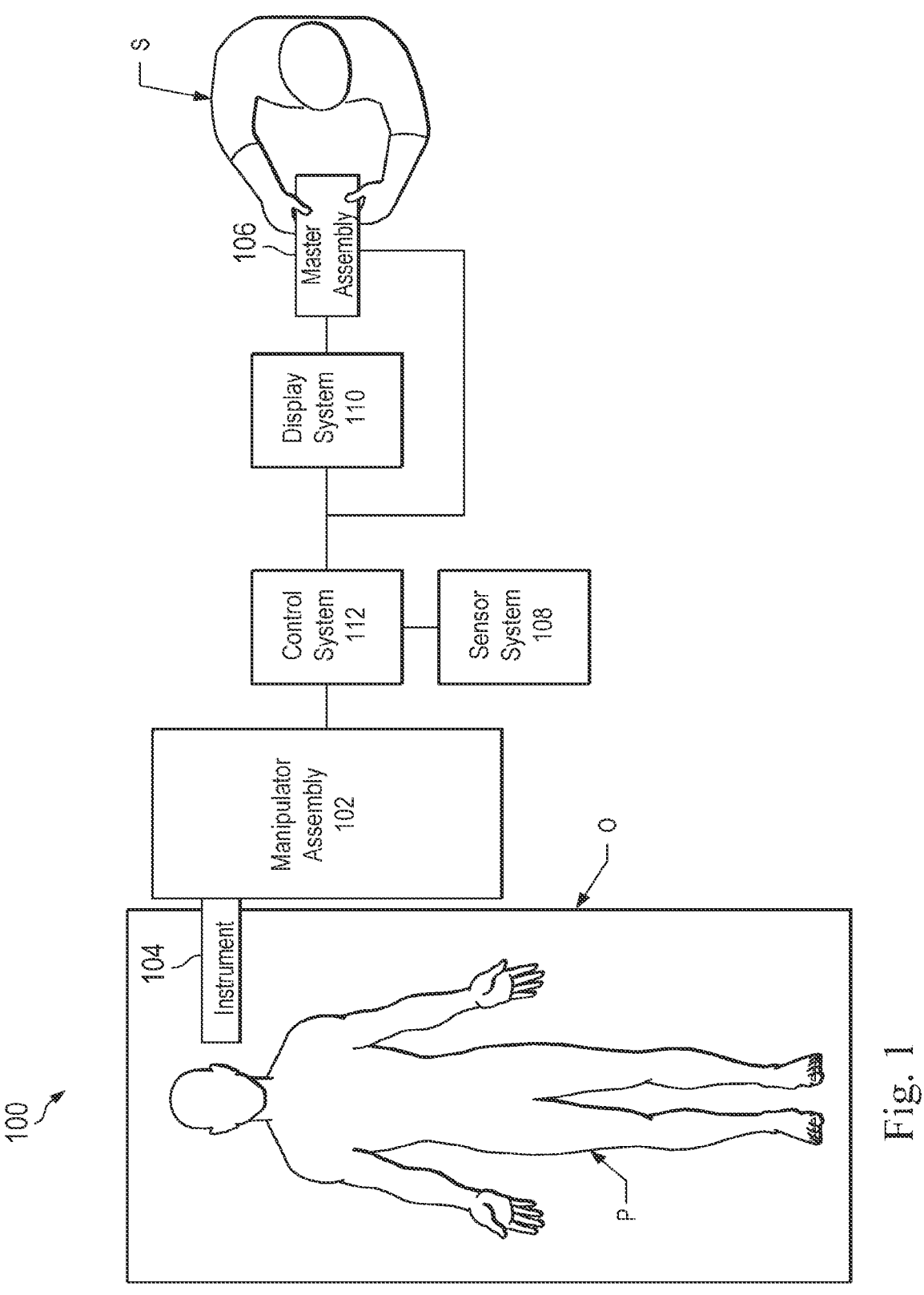
FIG. 1 is a simplified diagram of a teleoperated medical system according to some embodiments.

Embodiments of the present disclosure and their advantages are best understood by referring to the detailed description that follows. It should be appreciated that like reference numerals are used to identify like elements illustrated in one or more of the figures, wherein showings therein are for purposes of illustrating embodiments of the present disclosure and not for purposes of limiting the same.

DETAILED DESCRIPTION

In the following description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

In some instances well known methods, procedures, components, and circuits have not been described in detail so as not to unnecessarily obscure aspects of the embodiments.

This disclosure describes various instruments and portions of instruments in terms of their state in three-dimensional space. As used herein, the term "position" refers to the location of an object or a portion of an object in a three-dimensional space (e.g., three degrees of translational freedom along Cartesian x-, y-, and z-coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

Various lung bronchoscopic procedures involve navigating a flexible catheter in proximity of a lesion or tumor within the lungs under endoscopic guidance. Once near the target lesion, a procedure can be performed such as a biopsy where a biopsy needle can be delivered within a lumen of the flexible catheter to obtain a sample of the lesion tissue which is analyzed to, for example, determine whether it is cancerous or non-cancerous. While rough guidance to the target anatomy is performed with endoscopic visualization and the biopsy is often performed under fluoroscopy, in the case where the lesion is embedded within the parenchymal tissue, it is difficult to view and locate the lesion visually in either endoscopic or fluoroscopic images. Thus it can be difficult to verify whether a biopsy showing non-cancerous tissue is a result of a patient being cancer free or a result of the biopsy needle simply missing the lesion.

One way of being able to visualize a lesion in real time during a procedure is to use an endo-brachial ultrasound (EBUS) probe located near the target anatomy, such as by placement near the target anatomy and within an airway of the lung. Ultrasound, however, does not generally provide usable images through air, so one option is to block an airway of the lung by activating a sealing device collapsing one or more airways distal to the sealing device and thus collapsing a portion of the lung containing the lesion, and then using ultrasound to visualize the target anatomy. With a real time image of the lesion provided by the ultrasound, a biopsy (or another procedure) may be performed where the operator can accurately see the needle penetrate a lesion and confirm that target tissue was accessed and biopsied. Additional procedures, such as ablation, cryotherapy, drug delivery, and/or the like may benefit as well from similar visualization.

A few challenges may be expected with this visualization procedure. In general, the ultrasound transducer should be positioned within a range of the target anatomy (e.g., within about 5 cm or so) and should be positioned to capture images of the lesion within the target anatomy. Without suitably localizing the ultrasound transducer to both the target anatomy and the medical instrument to be directed by the ultrasound images, the relative positions of the ultrasound transducer and medical instrument may not be adequately known. This may result in the operator having to repeatedly position the transducer, collapse the lung to view with ultrasound, relate the lung to insert, retract, and/or rotate the ultrasound transducer semi-blindly until the lesion and medical instrument path is adequately visible in the ultrasound field of view. Because movement of the ultrasound transducer is more difficult in a collapsed lung, the operator would ideally prefer to position the ultrasound transducer in a suitable location within proximity to the lesion prior to collapsing the lung. Thus it would be advantageous to know the position and rotation of the ultrasonic transducer field of view relative to the lesion and the medical instrument prior to collapsing the lung so that as much of the positioning and alignment of the ultrasound transducer as possible may occur prior collapsing the lung. Thus a system providing stable positioning, accurate real-time localization, and controllable manipulation of the ultrasound transducer and the medical instrument during a procedure would be desirable.

FIG. 1 is a simplified diagram of a teleoperated medical system 100 according to some embodiments. In some embodiments, teleoperated medical system 100 may be suitable for use in, for example, surgical, diagnostic, therapeutic, or biopsy procedures within passageways of a patient's anatomy, such as the airways of lungs. As shown in FIG. 1, medical system 100 generally includes a teleoperational manipulator assembly 102 for operating one or more medical devices 104 in performing various procedures on a patient P. Teleoperational manipulator assembly 102 is mounted to or near an operating table O. A master assembly 106 allows a physician, clinician, or operator S to view the interventional site and to control teleoperational manipulator assembly 102.

Master assembly 106 may be located at an operator's console which is usually located in the same room as operating table O, such as at the side of a surgical table on which patient P is located. However, it should be understood that operator S can be located in a different room or a completely different building from patient P. Master assembly 106 generally includes one or more control devices for controlling teleoperational manipulator assembly 102. The control devices may include any number of a variety of input devices, such as joysticks, trackballs, data gloves, trigger-guns, hand-operated controllers, voice recognition devices, body motion or presence sensors, and/or the like. To provide operator S a strong sense of directly controlling the one or more medical devices 104, the control devices may be provided with the same degrees of freedom as the associated one or more medical devices 104. In this manner, the control devices provide operator S with telepresence or the perception that the control devices are integral with the one or more medical devices 104.

In some embodiments, the control devices may have more or fewer degrees of freedom than the associated one or more medical devices 104 and still provide operator S with telepresence. In some embodiments, the control devices may optionally be manual input devices which move with six degrees of freedom, and which may also include an actuatable handle for actuating instruments (for example, for closing grasping jaws, applying an electrical potential to an electrode, delivering a medicinal treatment, and/or the like).

Teleoperational manipulator assembly 102 supports the one or more medical devices 104 and may include a kinematic structure of one or more non-servo controlled links (e.g., one or more links that may be manually positioned and locked in place, generally referred to as a set-up structure) and a teleoperational manipulator. Teleoperational manipulator assembly 102 may optionally include a plurality of actuators or motors that drive inputs on the one or more medical devices 104 in response to commands from the control system (e.g., a control system 112). The actuators may optionally include drive systems that when coupled to one or more medical devices 104 may advance the one or more medical devices 104 into a naturally or surgically created anatomic orifice. Other drive systems may move the distal end of each of the one or more medical devices 104 in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the actuators can be used to actuate an articulable end effector of each of the one or more medical devices 104 for grasping tissue in the jaws in a gripper, taking a tissue sample with a biopsy device, orienting an ultrasound transducer, closing a passageway, and/or the like. Actuator position sensors such as resolvers, encoders, potentiometers, and other mechanisms may provide sensor data to medical system 100 describing the rotation and orientation of the motor shafts. This position sensor data may be used to determine motion of the objects manipulated by the actuators.

Teleoperated medical system 100 may include a sensor system 108 with one or more sub-systems for receiving information about the instruments of teleoperational manipulator assembly 102. Such sub-systems may include a positioning system including an electromagnetic (EM) sensor system, a shape sensor system, and/or the like for determining the pose (position and orientation), speed, velocity, pose, and/or shape of a distal end and/or of one or more segments along a flexible body that may make up each of the one or more medical devices 104; and/or a visualization system for capturing images.

Teleoperated medical system 100 also includes a display system 110 for displaying an image or representation of the surgical site (or site for a procedure) and the one or more medical devices 104 generated by sub-systems of sensor system 108. Display system 110 and master assembly 106 may be oriented so operator S can control the one or more medical devices 104 and master assembly 106 with the perception of telepresence.

In some embodiments, the one or more medical devices 104 may have a visualization system (discussed in more detail below), which may include a viewing scope assembly that records a concurrent or real-time image of a surgical site and provides the image to the clinician or operator S through one or more displays of medical system 100, such as one or more displays of display system 110. The concurrent image may be, for example, a two or three dimensional image captured by an endoscope positioned within the surgical site. In some embodiments, the visualization system includes endoscopic components that may be integrally or removably coupled to the one or more medical devices 104. However in some embodiments, a separate endoscope, attached to a separate manipulator assembly may be used with the one or more medical devices 104 to image the surgical site. In some embodiments, the visualization system may include an ultrasound transducer located at or near a distal end of one of the one or more medical devices 104. The visualization system may be implemented as hardware, firmware, software or a combination thereof which interact with or are otherwise executed by one or more computer processors, which may include the processors of a control system 112. The processors of control system 112 may execute instructions comprising instruction corresponding to processes disclosed herein and described in more detail below.

Display system 110 may also display one or more images of the surgical site and medical instruments captured by the visualization system. In some examples, teleoperated medical system 100 may configure the one or more medical devices 104 and controls of master assembly 106 such that the relative positions of the medical devices 104 are similar to the relative positions of the eyes and hands of operator S. In this manner operator S can manipulate the one or more medical devices 104 and the hand control as if viewing the workspace in substantially true presence. By true presence, it is meant that the presentation of an image is a true perspective image simulating the viewpoint of an operator that is physically manipulating the one or more medical devices 104.

In some examples, display system 110 may present images of a surgical site recorded pre-operatively or intra-operatively using image data from imaging technology such as, computed tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like. The pre-operative or intra-operative image data may be presented as two-dimensional, three-dimensional, or four-dimensional (including e.g., time based or velocity based information) images and/or as images from models created from the pre-operative or intra-operative image data sets.

In some embodiments, often for purposes of imaged guided surgical or medical procedures, display system 110 may display a virtual navigational image in which the actual locations of the one or more medical devices 104 are registered (i.e., dynamically referenced) with the preoperative or concurrent images/model. This may be done to present the clinician or operator S with a virtual image of the internal surgical site from a viewpoint of the one or more medical devices 104. In some examples, the viewpoint may be from a tip of one of the one or more medical devices 104, from the perspective of an ultrasound image, and/or the like. An image of the tips of the one or more medical devices 104 and/or other graphical or alphanumeric indicators may be superimposed on the virtual image to assist operator S controlling the one or more medical devices 104. In some examples, the one or more medical devices 104 may not be visible in the virtual image.

In some embodiments, display system 110 may display a virtual navigational image in which the actual locations of the one or more medical devices 104 are registered with preoperative or concurrent images to present the clinician or operator S with a virtual image of the one or more medical devices 104 within the surgical site from an external viewpoint. An image of a portion of the one or more medical devices 104 or other graphical or alphanumeric indicators may be superimposed on the virtual image to assist operator S in the control of the one or more medical devices 104.

Teleoperated medical system 100 may also include control system 112. Control system 112 includes at least one memory and at least one computer processor (not shown) for effecting control between the one or more medical devices 104, master assembly 106, sensor system 108, and display system 110. Control system 112 also includes programmed instructions (e.g., a non-transitory machine-readable medium storing the instructions) to implement some or all of the methods described in accordance with aspects disclosed herein, including instructions fix providing information to display system 110. While control system 112 is shown as a single block in the simplified schematic of FIG. 1, the system may include two or more data processing circuits with one portion of the processing optionally being performed on or adjacent to teleoperational manipulator assembly 102, another portion of the processing being performed at master assembly 106, and/or the like. Any of a wide variety of centralized or distributed data processing architectures may be employed. Similarly the programmed instructions may be implemented as a number of separate programs or subroutines, or they may be integrated into a number of other aspects of the teleoperational systems described herein. In one embodiment, control system 112 supports wireless communication protocols such as Bluetooth, IrDA, HomeRF, IEEE 802.11, DECT, and Wireless Telemetry.

In some embodiments, control system 112 may transmit signals instructing one or more actuators of teleoperational manipulator assembly 102 to move the one or more medical devices 104. The one or more medical devices 104 may extend into an internal surgical or medical site within the body of patient P via openings in the body of patient P. Any suitable conventional and/or specialized actuators may be used. In some examples, the one or more actuators may be separate from, or integrated with, teleoperational manipulator assembly 102. In some embodiments, the one or more actuators and teleoperational manipulator assembly 102 are provided as part of a teleoperational cart positioned adjacent to patient P and operating table O.

Control system 112 may optionally further include a virtual visualization system to provide navigation assistance to operator S when controlling the one or more medical devices 104 during an image-guided medical procedure. Virtual navigation using the virtual visualization system may be based upon reference to an acquired preoperative or intraoperative dataset of anatomic passageways. The virtual visualization system processes images of the medical site imaged using imaging technology such as CT, MRI, fluoroscopy, thermography, ultrasound, OCT, thermal imaging, impedance imaging, laser imaging, nanotube X-ray imaging, and/or the like. Software, which may be used in combination with manual inputs, is used to convert the recorded images into segmented two dimensional or three dimensional composite representation of a partial or an entire anatomic organ or anatomic region. An image data set is associated with the composite representation. The composite representation and the image data set describe the various locations and shapes of the passageways and their connectivity, The images used to generate the composite representation may be recorded preoperatively or intra-operatively during a clinical procedure. In some embodiments, a virtual visualization system may use standard representations (i.e., not patient specific) or hybrids of a standard representation and patient specific data. The composite representation and any virtual images generated by the composite representation may represent the static posture of a deformable anatomic region during one or more phases of motion (e.g., during an inspiration/expiration cycle of a lung).

During a virtual navigation procedure, sensor system 108 may be used to compute approximate locations of the one or more medical devices 104 with respect to the anatomy of patient P. The location can be used to produce both macrolevel (external) tracking images of the anatomy of patient P and virtual internal images of the anatomy of patient P. The system may implement one or more electromagnetic (EM) sensor, fiber optic sensors, and/or other sensors to register and display a medical implement together with preoperatively recorded surgical images, such as those from a virtual visualization system, are known. For example U.S. patent application Ser. No. 13/107,562 (filed May 13, 2011) (disclosing "Medical System Providing Dynamic Registration of a Model of an Anatomic Structure for Image-Guided Surgery") which is incorporated by reference herein in its entirety, discloses one such system. Teleoperated medical system 100 may further include optional operations and support systems (not shown) such as illumination systems, steering control systems, irrigation systems, and/or suction systems. In some embodiments, teleoperated medical system 100 may include more than one teleoperational manipulator assembly and/or more than one master assembly. The exact number of teleoperational manipulator assemblies will depend on the medical procedure and the space constraints within the operating room, among other factors. In some examples, multiple master assemblies allow more than one operator to control one or more teleoperational manipulator assemblies in various combinations.

Figure 2:
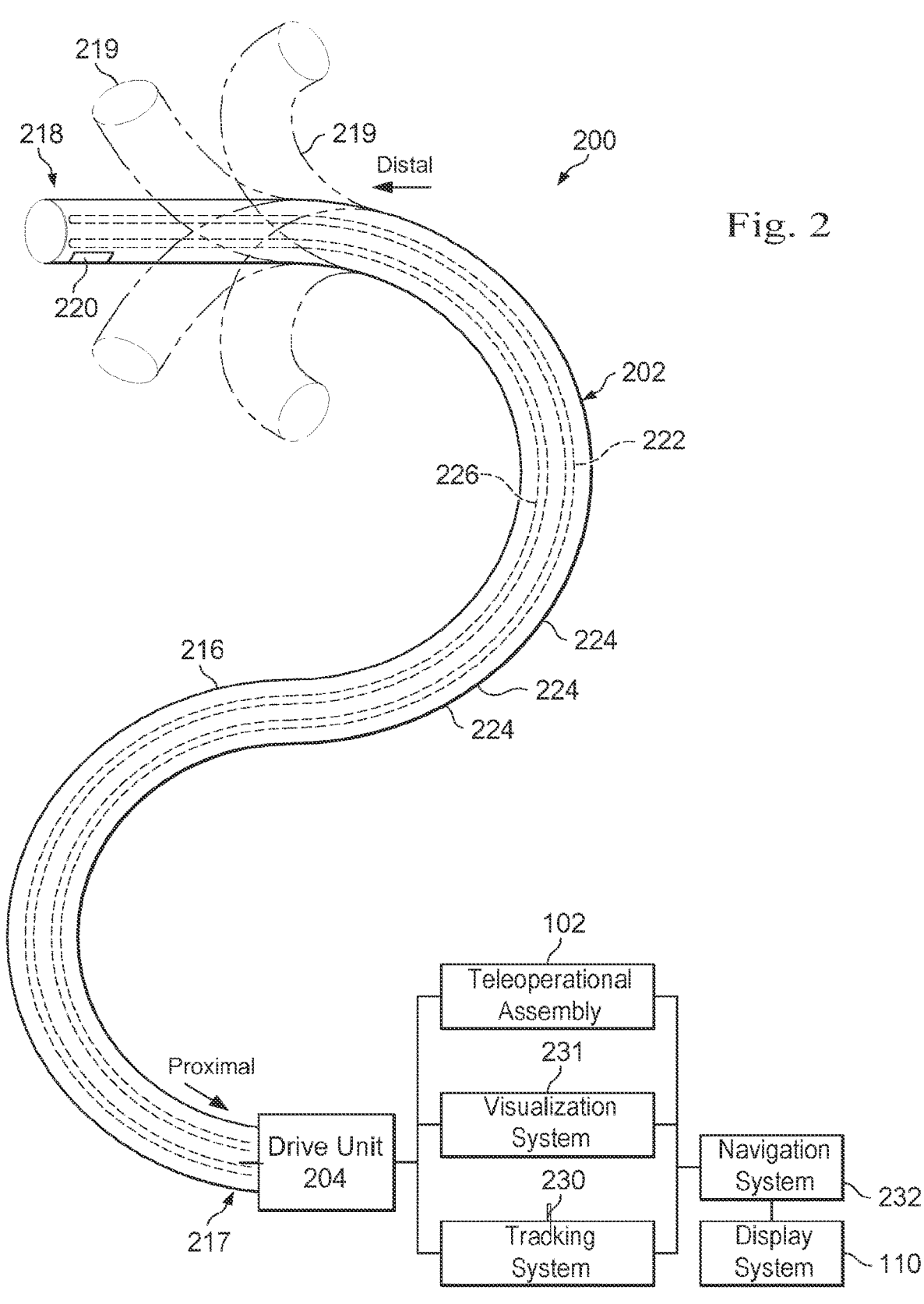
FIG. 2 is a simplified diagram of a medical instrument system according to some embodiments.

FIG. 2 is a simplified diagram of a medical instrument system 200 according to some embodiments. In some embodiments, medical instrument system 200 may be used as any of the one or more medical devices 104 in an image-guided medical procedure performed with teleoperated medical system 100. In some examples, medical instrument system 200 may be used for non-teleoperational exploratory procedures or in procedures involving traditional manually operated medical instruments, such as endoscopy.

Medical instrument system 200 includes an elongate instrument 202 coupled to a drive unit 204. Elongate instrument 202 includes a flexible body 216 having proximal end

217 and distal end 218 (also "tip portion 218.") In some embodiments, flexible body 216 has an approximately 3 mm outer diameter. Other flexible body outer diameters may be larger or smaller. Elongate instrument 202 may optionally include shape sensor 222 for determining the position, orientation, speed, velocity, pose, and/or shape of the catheter tip at distal end 218 and/or of one or more segments 224 along flexible body 216. The entire length of flexible body 216, between distal end 218 and proximal end 217, may be effectively divided into segments 224. If medical instrument system 200 is one of the one or more medical devices 104 of a teleoperated medical system 100, shape sensor 222 may be a component of sensor system 108. If medical instrument system 200 is manually operated or otherwise used for non-teleoperational procedures, shape sensor 222 may be coupled to a tracking system 230 that interrogates shape sensor 222 and processes received shape data.

Shape sensor 222 may optionally include an optical fiber aligned with flexible body 216 (e.g., provided within an interior channel (not shown) or mounted externally). In some embodiments, the optical fiber has a diameter of approximately 200 μm. In some embodiments, the dimensions may be larger or smaller. The optical fiber of shape sensor 222 forms a fiber optic bend sensor for determining the shape of elongate instrument 202. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. patent application Ser. No. 11/180,389 (filed Jul. 13, 2005) (disclosing "Fiber optic position and shape sensing device and method relating thereto"); U.S. patent application Ser. No. 12/047,056 (filed on Jul. 16, 2004) (disclosing "Fiber-optic shape and relative position sensing"); and U.S. Pat. No. 6,389,187 (filed on Jun. 17, 1998) (disclosing "Optical Fibre Bend Sensor"), which are all incorporated by reference herein in their entireties. Sensors in some embodiments may employ other suitable strain sensing techniques, such as Rayleigh scattering, Raman scattering, Brillouin scattering, and Fluorescence scattering. In some embodiments, the shape of the catheter may be determined using other techniques. For example, a history of the distal end pose of elongate instrument 202 can be used to reconstruct the shape of flexible body 216 over the interval of time. As another example, historical pose, position, or orientation data may be stored for a known point of an instrument system along a cycle of alternating motion, such as breathing. This stored data may be used to develop shape information about flexible body 216. In some examples, a series of positional sensors, such as electromagnetic (EM) sensors, positioned along flexible body 216 can be used for shape sensing. In some examples, a history of data from a positional sensor, such as an EM sensor, on the instrument system during a procedure may be used to represent the shape of the instrument, particularly if an anatomic passageway is generally static. In some examples, a wireless device with position or orientation controlled by an external magnetic field may be used for shape sensing. The history of the position of the wireless device may be used to determine a shape for the navigated passageways.

In some embodiments, medical instrument system 200 may, optionally, include position sensor system 220, Position sensor system 220 may be a component of an EM sensor system with positional sensor system 220 including one or more conductive coils that may be subjected to an externally generated electromagnetic field. Each coil of EM sensor system used to implement positional sensor system 220 then produces an induced electrical signal having characteristics that depend on the position and orientation of the coil relative to the externally generated electromagnetic field. In some embodiments, an EM sensor system used to implement the positional sensor system 220 may be configured and positioned to measure six degrees of freedom, e.g., three position coordinates X, Y, Z and three orientation angles indicating pitch, yaw, and roll of a base point or five degrees of freedom, e.g., three position coordinates X, Y, Z and two orientation angles indicating pitch and yaw of a base point. Further description of an EM sensor system is provided in U.S. Pat. No. 6,380,732 (filed Aug. 11, 1999) (disclosing "Six-Degree of Freedom Tracking System Having a Passive Transponder on the Object Being Tracked"), which is incorporated by reference herein in its entirety. In some embodiments, shape sensor 222 may also function as the position sensor because the shape of shape sensor 222 together with information about the location of the base of shape sensor 222 (in the fixed coordinate system of patient P) allows the location of various points along shape sensor 222, including distal end 218, to be determined.

In some embodiments, tracking system 230 may optionally include position sensor system 220 and shape sensor 222 for determining the position, orientation, speed, pose, and/or shape of distal end 218 and of one or more segments 224 of medical instrument system 200. Tracking system 230 may optionally be implemented as hardware, firmware, software or a combination thereof which interact with or are otherwise executed by one or more computer processors, which may include the processors of control system 112 in FIG. 1.

In some embodiments, flexible body 216 includes one or more lumens 226 sized and shaped to receive corresponding medical instruments. The medical instruments may include, for example, image capture probes, biopsy instruments, ablation devices, cryotherapeutic devices, drug delivery needles, and/or other surgical, diagnostic, or therapeutic tools. The ablation devices may include bipolar or monopolar devices using microwave energy, radio frequency, electrodes, ultrasound transducers, and/or the like. In some examples, the medical instrument may provide bipolar or monopolar radio frequency energy, microwave energy, ultrasound, cryotherapeutic energy, chemicals, direct heat and/or the like. Other end effectors may further include electrically activated end effectors such as electrosurgical electrodes, transducers, sensors, and/or the like.

In some embodiments, the medical instrument system 202 may include an image capture probe that includes a distal portion with a stereoscopic or monoscopic camera at or near distal end 218 of flexible body 216 for capturing images (including video images) that are processed by a visualization system 231 for display. The image capture probe may include a cable coupled to the camera for transmitting the captured image data. In some examples, the image capture instrument may be a fiber-optic bundle, such as a fiberscope, that couples to visualization system 231. In some examples the captured image data may be transmitted using Bluetooth, WiFi, or other remote data. transmission technology. The image capture instrument may be single or multi-spectral, for example capturing image data in one or more of the visible, infrared, and/or ultraviolet spectrums.

In some embodiments, the medical instrument system 202 may include an ultrasound transducer located at or near distal end 218 of flexible body 216 for capturing ultrasound images in the region of distal end 218. In some examples, the elongate instrument 202 may be rotated about the longitudinal axis of flexible body 216 to allow the ultrasound transducer to obtain ultrasound images in a field of view located near distal end 218. The ultrasound transducer may be coupled to one or more electrical wires or optical fibers for activating the ultrasound transducer, modulating its output, capturing return signals, and/or the like. In some examples, ultrasound imaging devices may include side-facing transducers, forward-facing transducers, curved transducers, and/or the like. In some examples, the ultrasonic imaging device may consist of one or more electronically phased, mechanically scanned, and/or mechanically steerable transducer elements and/or arrays of transducer elements that are capable of capturing 2D, 3D, and/or 4D ultrasound images in proximity to distal end 218.

In some examples, the ultrasound transducer may be included in a medical instrument, such as a needle, that may be extended beyond distal end 218 and optionally inserted into the solid anatomy of the patient. The ultrasound transducer may be included in an imaging probe configured to be received within one of the lumens 226 of the elongate instrument 202. In some examples, the imaging probe may be a radial probe or a radial EFILIS probe that may be rotated about the longitudinal axis of the radial probe to allow the ultrasound transducer to obtain ultrasound images in a field of view located near distal end 218. In some examples, the imaging probe may include ultrasound transducers configured to be side-facing, forward-facing, curved, and/or the like. In some examples the imaging probe may include ultrasound transducers which include a plurality of phased array transducer elements which are electronically phased to capture 2D, 3D, and/or 4D ultrasound images.

The medical instrument may additionally house cables, linkages, and/or other actuation controls (not shown) that extend between proximal end 217 and distal end 218 to controllably bend and/or actuate a distal end of the medical device inserted through one of the lumens 226. Steerable instruments are described in detail in U.S. Pat. No. 7,316, 681 (filed on Oct. 4, 2005) (disclosing "Articulated Surgical Instrument for Performing Minimally invasive Surgery with Enhanced Dexterity and Sensitivity") and U.S. patent application Ser. No. 12/286,644 (filed Sep. 30, 2008) (disclosing "Passive Preload and Capstan Drive for Surgical Instruments"), which are incorporated by reference herein in their entireties.

Flexible body 216 may also house cables, linkages, or other steering controls (not shown) that extend between drive unit 204 and distal end 218 to controllably bend distal end 218 as shown, for example, by broken dashed line depictions 219 of distal end 218. In some examples, at least four cables are used to provide independent "up-down" steering to control a pitch of distal end 218 and "left-right" steering to control a yaw of distal end 218. Steerable catheters are described in detail in U.S. patent application Ser. No. 13/274,208 (filed Oct. 14, 2011) (disclosing "Catheter with Removable Vision Probe"), which is incorporated by reference herein in its entirety. In embodiments in which medical instrument system 200 is actuated by a teleoperational assembly, drive unit 204 may include drive inputs that removably couple to and receive power from drive elements, such as actuators, of the teleoperational assembly. In some embodiments, medical instrument system 200 may include gripping features, manual actuators, or other components for manually controlling the motion of medical instrument system 200. Elongate instrument 202 may be steerable or, alternatively, the system may be non-steerable with no integrated mechanism for operator control of the bending of distal end 218. In some examples, one or more lumens, through which medical instruments can be slideably deployed and used at a target anatomical location, are defined in the walls of flexible body 216.

In some embodiments, medical instrument system 200 may include a flexible bronchial instrument, such as a bronchoscope or bronchial catheter, for use in examination, diagnosis, biopsy, or treatment of a lung. Medical instrument system 200 is also suited for navigation and treatment of other tissues, via natural or surgically created connected passageways, in any of a variety of anatomic systems, including the colon, the intestines, the kidneys and kidney calices, the brain, the heart, the circulatory system including vasculature, and/or the like.

In some embodiments, medical instrument system 200 may include a sealing device having one or more expandable bladders or balloons (not shown) located at one or more positions along the outside of flexible body 216. By injecting air, saline, and/or some other gas or fluid, the one or more balloons may be expanded and/or collapsed to create a temporary closure in the passageway in which flexible body 216 is inserted. In some examples, a shape of each of the one or more balloons upon expanding is malleable, allowing each of the one or more balloons to conform to a shape of the passageway, to expand around other medical devices in the passageway, and/or the like. In some examples, each of the one or more balloons may optionally include a valve, flap, siphon tube, and/or the like allowing evacuation of air within the passageway distal to the one or more balloons, thus collapsing the passageway around any medical instruments located distal to the one or more balloons.

The information from tracking system 230 may be sent to a navigation system 232 where it is combined with information from visualization system 231 and/or the preoperatively obtained models to provide the operator or other operator with real-time position information. In some examples, the real-time position information may be displayed on display system 110 of FIG. 1 for use in the control of medical instrument system 200 In some examples, control system 116 of FIG. 1 may utilize the position information as feedback for positioning medical instrument system 200. Various systems for using fiber optic sensors to register and display a medical instrument with surgical images are provided in U.S. patent application Ser. No. 13/107,562, filed May 13, 2011, disclosing, "Medical System Providing Dynamic Registration of a Model of an Anatomic Structure for Image-Guided Surgery," which is incorporated by reference herein in its entirety.

In some examples, medical instrument system 200 may be teleoperated within medical system 100 of FIG. 1. In some embodiments teleoperational manipulator assembly 102 of FIG. 1 which may include various handles and operator interfaces for hand-held operation of the instrument.

Figure 3:
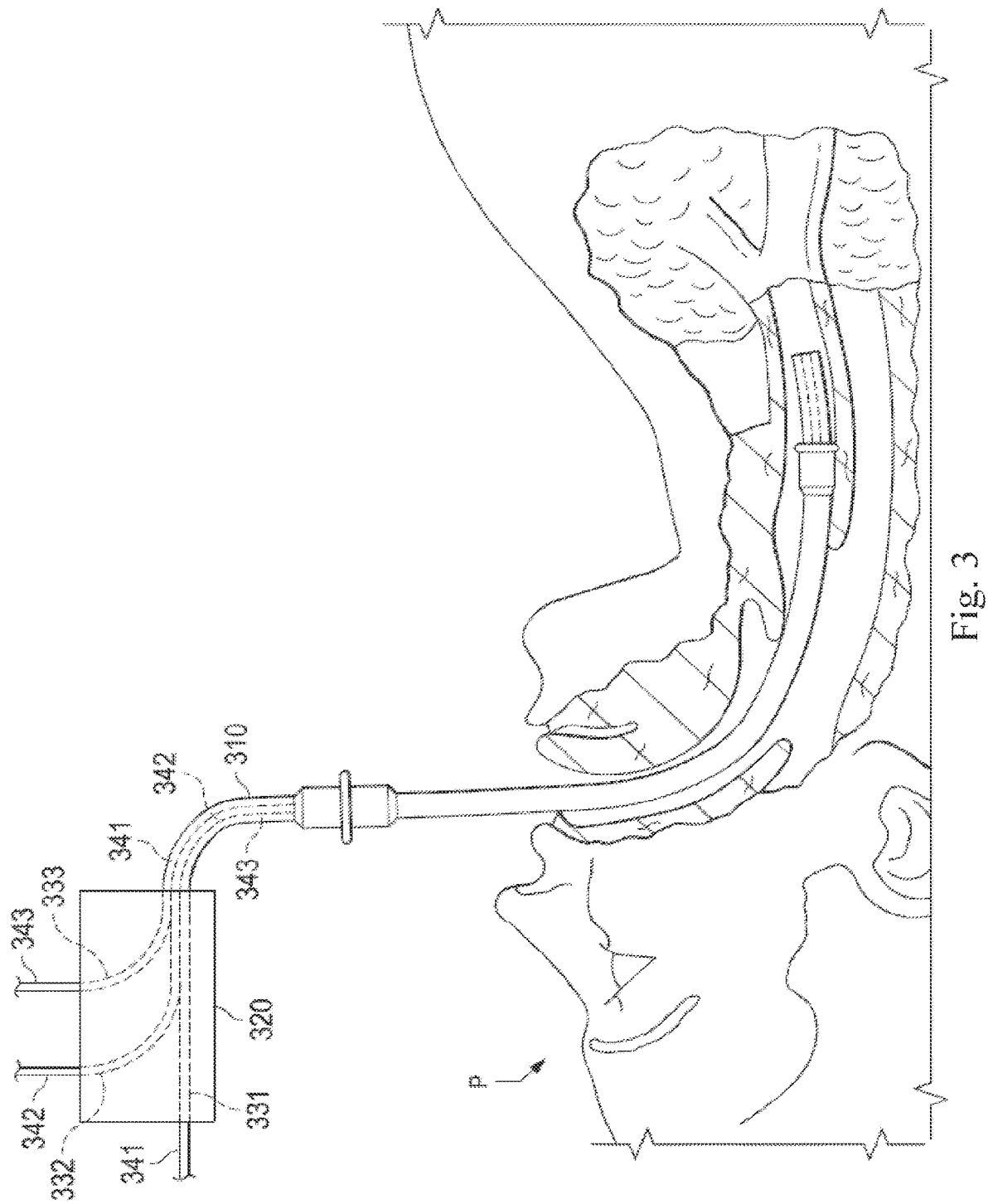
FIG. 3 is a simplified diagram of medical instruments being introduced into a patient according to some embodiments.

FIG. 3 is a simplified diagram of medical instruments being introduced into a patient P according to some embodiments. As shown in FIG. 3, an endotracheal (ET) tube 310 is used to introduce several medical instruments into the airways of patient P. In order for ET tube 310 to accommodate more than one medical instrument, a multi-port adaptor 320 is used to align the medical instruments for insertion through ET tube 310. As shown, adaptor 320 includes three insertion channels 331-333 for accepting three medical instruments 341-343. And although FIG. 3 shows only three insertion channels 331-333 and three medical instruments 341-343, one of ordinary skill that adaptor 320 may optionally include two channels or four or more channels. In some examples, each of the medical instruments 341-343 may be consistent with elongate instrument 202 of FIG. 2. As adaptor 320 further shows, each of the channels 331-333 is angled and/or curved to help direct the distal ends of medical instruments 341-343 into one or more lumens of a flexible catheter and/or ET tube 310. In some embodiments, each of the insertion channels 331-333 may include a sealing mechanism (not shown) so as to prevent air from the lungs of patient P from flowing around each of the medical instruments 341-343.

Figure 4A:
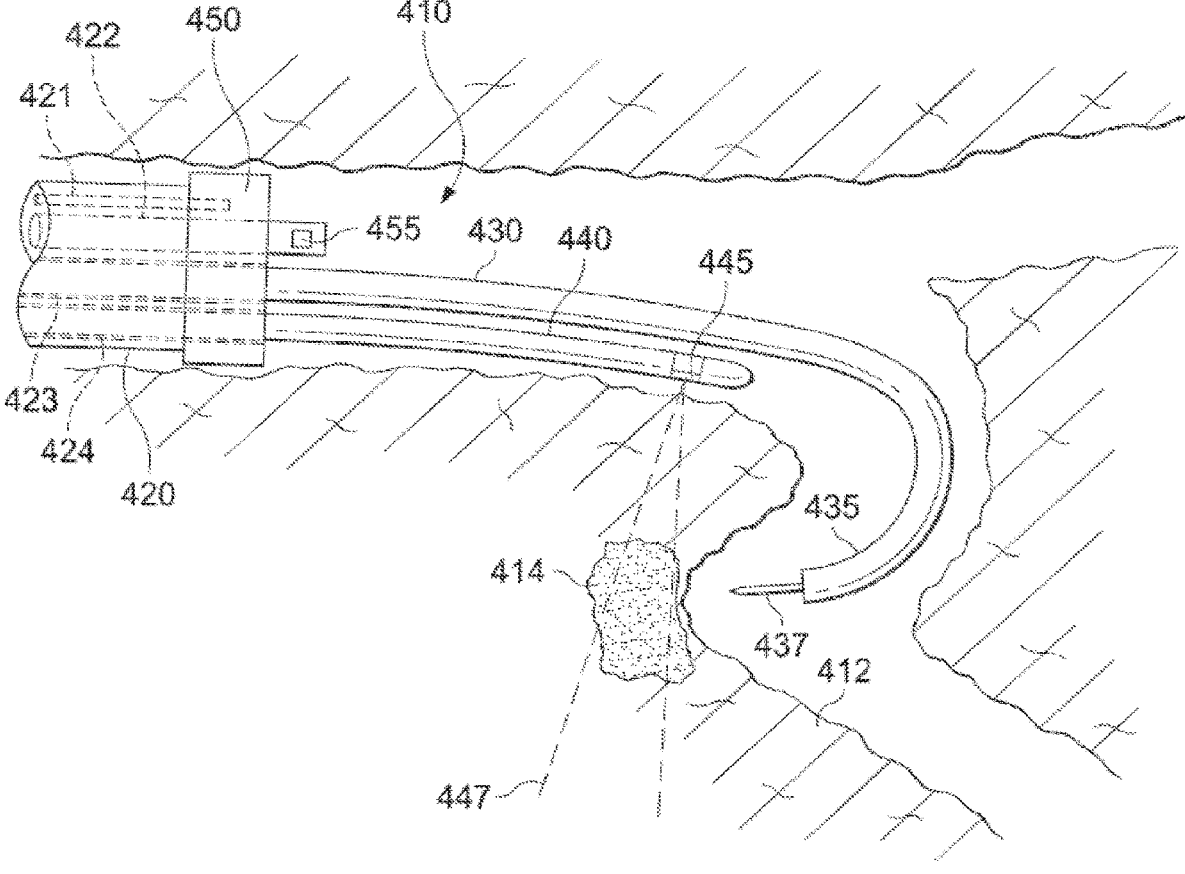
FIGS. 4A and 4B are simplified diagrams of side view of medical instruments within patient anatomy according to some embodiments.
Figures 4B, 4C:
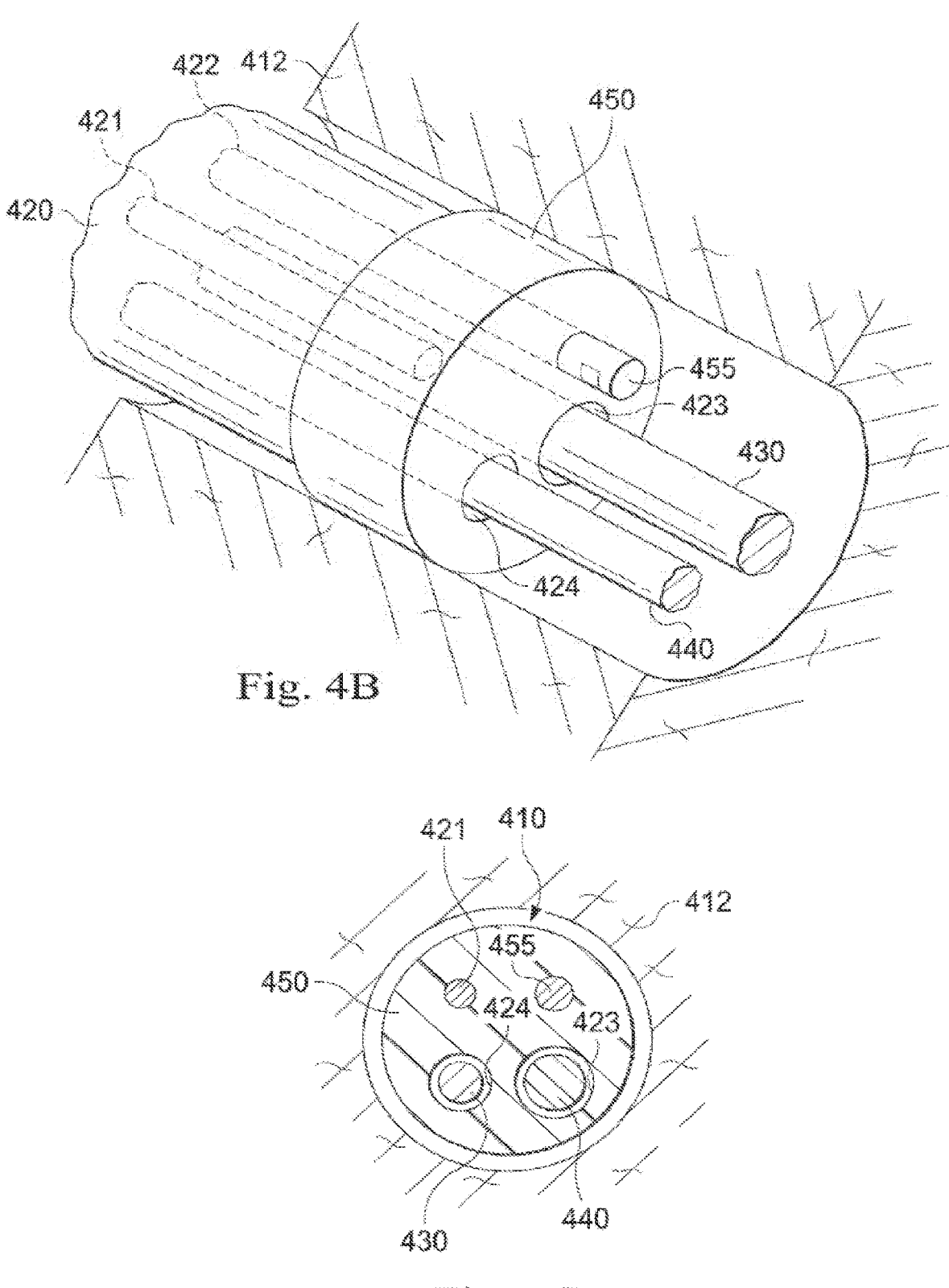
FIG. 4C is a simplified diagram of a cut-away view of the medical instruments and patient anatomy of FIG. 4B according to some embodiments.

FIGS. 4A and 4B are simplified diagrams of side views of medical instruments within patient anatomy according to some embodiments. As shown in FIG. 4A, the patient anatomy includes a plurality of passageways 410 surrounded by tissue 412 prior to collapsing of passageways 410 distal to a seal point within passageways 410 as is described further below. In some examples, passageways 410 may correspond to airways of a patient's lungs. Located within tissue 412 is a region of interest 414, which may correspond to a lesion, a tumor, and/or the like. Thus, the region of interest 414 may also be referred to herein as a lesion 414 or a tumor 414. As further shown, passageways 410 are not collapsed, and have inserted into them several medical instruments. In some examples, one or more of the medical instruments may be consistent with elongate instrument 202.

Delivery of the one or medical instruments within passageways 410 in the vicinity of lesion 414 is accomplished using an instrument catheter 420 having multiple lumens including an inflation lumen 421, an evacuation lumen 422, a working lumen 423, and an imaging lumen 424. In some examples, instrument catheter 420 is consistent with elongate instrument 202. Instrument catheter 420 may be steered so as to position instrument catheter 420 where desired within passageways 410. In some examples, a position sensor system (such as position sensor system 220) and/or a shape sensor (such as shape sensor 222) may be used to register instrument catheter 420 to one or more pre-operative or intra-operative images and/or models of the patient anatomy and to provide real time localization of instrument catheter 420 to help guide the operator in steering instrument catheter 420. In some examples, an endoscope and/or other imaging device may he inserted into instrument catheter 420 through working lumen 423 and may further be used to aid the operator in steering instrument catheter 420. Once in the desired location, instrument catheter 420 may be parked.

A working catheter 430 having one or more lumens (not shown) for introducing one or more medical instruments in proximity to lesion 414 may be inserted into passageways 410 through working lumen 423. Working catheter 430 includes a distal end 435, which may be steered so as to orient distal end 435 toward lesion 414. In some examples, a position sensor system (such as position sensor system 220) and/or a shape sensor (such as shape sensor 222) may be used to register working catheter 430 to one or more pre-operative or intra-operative images and/or models of the patient anatomy and to provide real time localization of working catheter 430 to help guide the operator in steering distal end 435 toward lesion 414. In some examples, an endoscope inserted through one of the lumens may further be used to aid the operator in positioning and/or orienting distal end 435. A biopsy needle 437 is shown extended beyond distal end 435 to allow a tissue sample to be taken, although in some examples, extension of biopsy needle 437 may be delayed until distal end 435 is properly positioned. In some examples, the endoscope and the biopsy needle 437 may simultaneously be inserted through lumens within working catheter 430. Alternatively, the endoscope can be used during navigation through anatomy toward lesion 414 where working catheter 430 may be parked. The endoscope may then be removed from working catheter 430 and replaced with biopsy needle 437.

An imaging probe 440 having located near its distal end one or more imaging elements 445 may be inserted into passageways 410 through imaging lumen 424. As shown, imaging probe 440 is positioned within passageways 410 where it is advantageous for the one or more imaging elements 445 to take intra-operative and real-time images of lesion 414. Similar to instrument catheter 420 and working catheter 430, a position sensor system and/or a shape sensor may be used to register imaging probe 440 to the one or more pre-operative or intra-operative images to provide real time localization of imaging probe 440 to help guide the operator in positioning and/or orienting the one or more imaging elements 445 to take images of lesion 414. In some examples, the one or more imaging elements 445 may alternatively or additionally be usable to capture images of working catheter 430, distal end 435, biopsy needle 437, and/or one or more fiducial markers located on working catheter 430 and/or biopsy needle 437 to aid in registering imaging probe 440 and/or localizing imaging probe 440 relative to lesion 414 and/or biopsy needle 437. As shown, the imaging probe 440 can include the one or more imaging elements 445 consistent with a transducer, where the imaging probe may be rotated along a longitudinal axis of the imaging probe 440 to capture images along an imaging field of view 447. In some examples, the one or more imaging elements 445 may be replaced by an array of imaging elements capable of capturing images in all directions around imaging probe 440 without having to rotate the imaging elements in the array. In practice, the one or more imaging elements 445 are positioned and oriented so that imaging field of view 447 passes through lesion 414 and is able to capture images of both lesion 414 and biopsy needle 437 as it penetrates lesion 414.

Inflation lumen 421 may be used to activate a sealing device which can include one or more balloons 450. The one or more balloons 450 may be used to create a seal across one of passageways 410 at a seal point prior to collapsing passageways 410 distal to the seal point. To create the seal, the one or more balloons 450 may be expanded and/or enlarged to fill the passageway 410 at the seal point. In some examples, air, saline, and/or some other gas or fluid is injected into the one or more balloons 450 through inflation lumen 421 to expand the one or more balloons 450. FIG. 4B is a simplified diagram of a cut-away view of the one or more balloons 450 expanded to fill one of the passageways 410 according to some embodiments. As shown in FIG. 4B, the one or more balloons 450 are expanded until they reach the tissue 412 surrounding the passageway 410 where they are sufficiently malleable to conform to the shape of the tissue 412 at the seal point. FIG. 4C is a simplified diagram of a cross-sectional view of the passageway 410 further showing the conformance in shape of the one or more balloons 450 about the passageway 410.

Figure 4D:
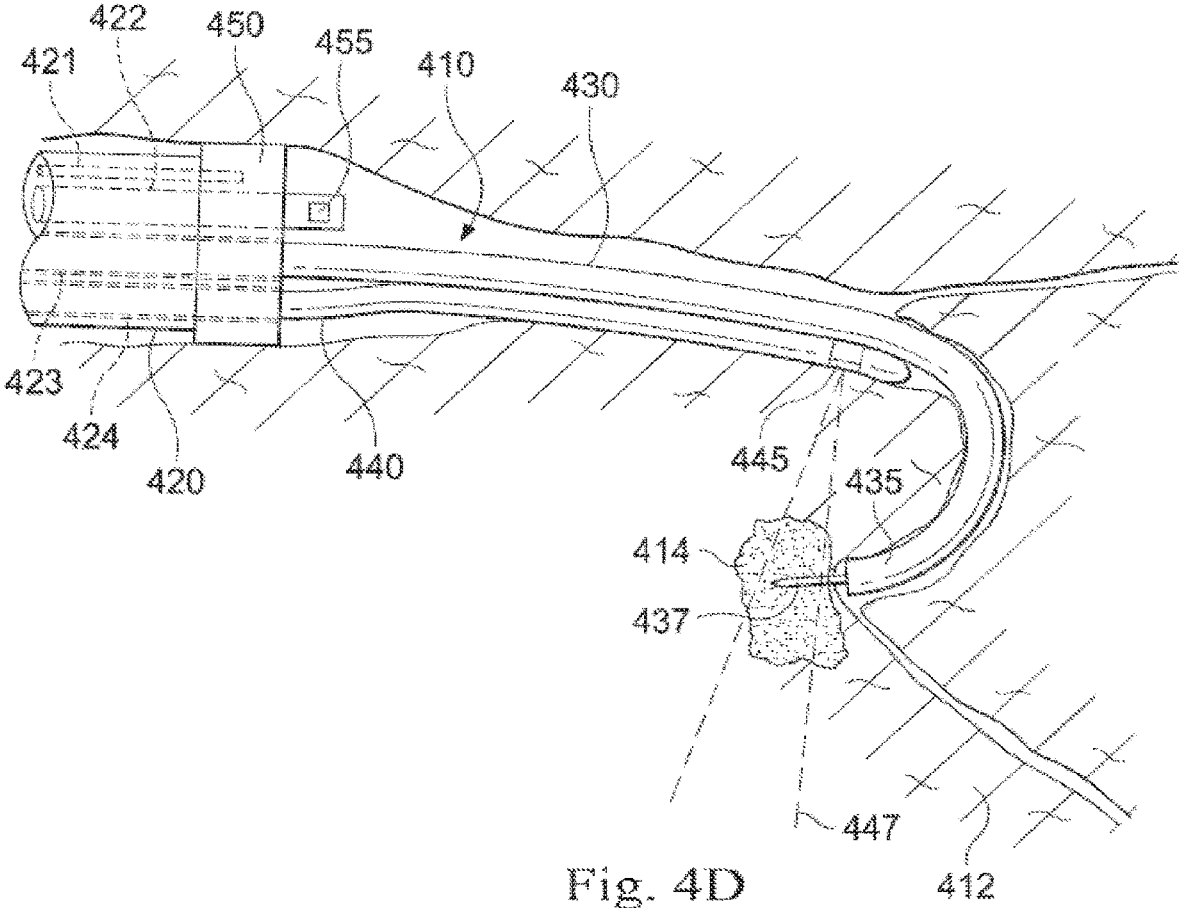
FIG. 4D is a simplified diagram of a cross-sectional views of the medical instruments and patient anatomy of FIG. 4B according to some embodiments.

Once passageway 410 is sealed, the passageways distal to the seal point are allowed to collapse about working catheter 430 and imaging probe 440 as shown in FIG. 4D. In some examples, an evacuation port 455 located at a distal end of evacuation lumen 422 may be used to remove air from passageways 410 distal to the one or more balloons 450 and the seal point. In some examples, a vacuum may be applied to evacuation lumen 422 to siphon air from passageways 410. In some examples, one or more valves, flaps, and/or the like (not shown) may be located at or near evacuation port 455 and/or along evacuation lumen 422 to aid in the siphoning of the air.

Figure 5:
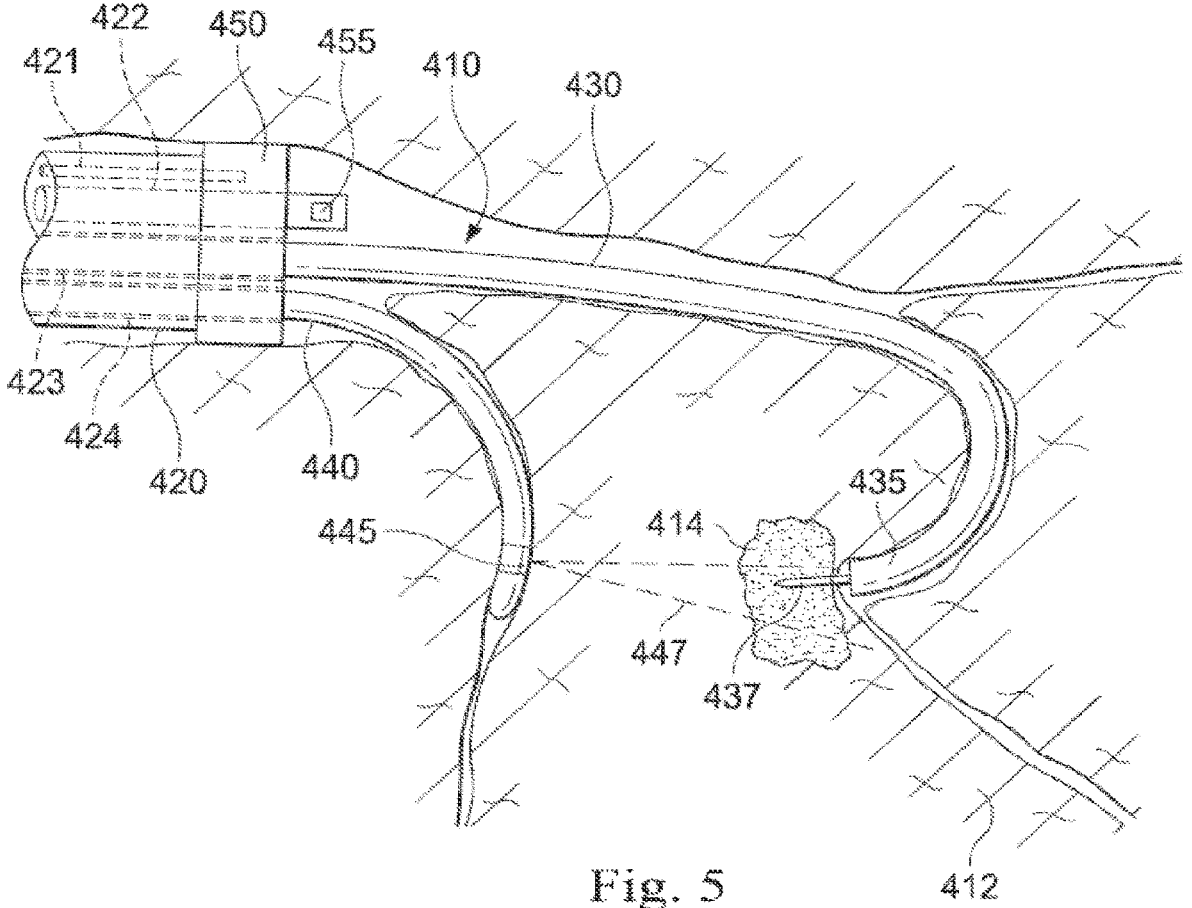
FIG. 5 is a simplified diagram of side views of medical instruments within patient anatomy according to some embodiments.

FIG. 5 is a simplified diagram of side views of medical instruments within patient anatomy according to some embodiments. As shown in FIG. 5, imaging probe 440 of FIGS. 4A and 4D is placed in a different branch of passageway 410 than working catheter 430. As long as the one or more imaging elements 445 are within range of lesion 414, are positionable and orientable to capture images of lesion 414, and are located distal to the one or more balloons 450, any combination of passageways may be used.

Figure 6:
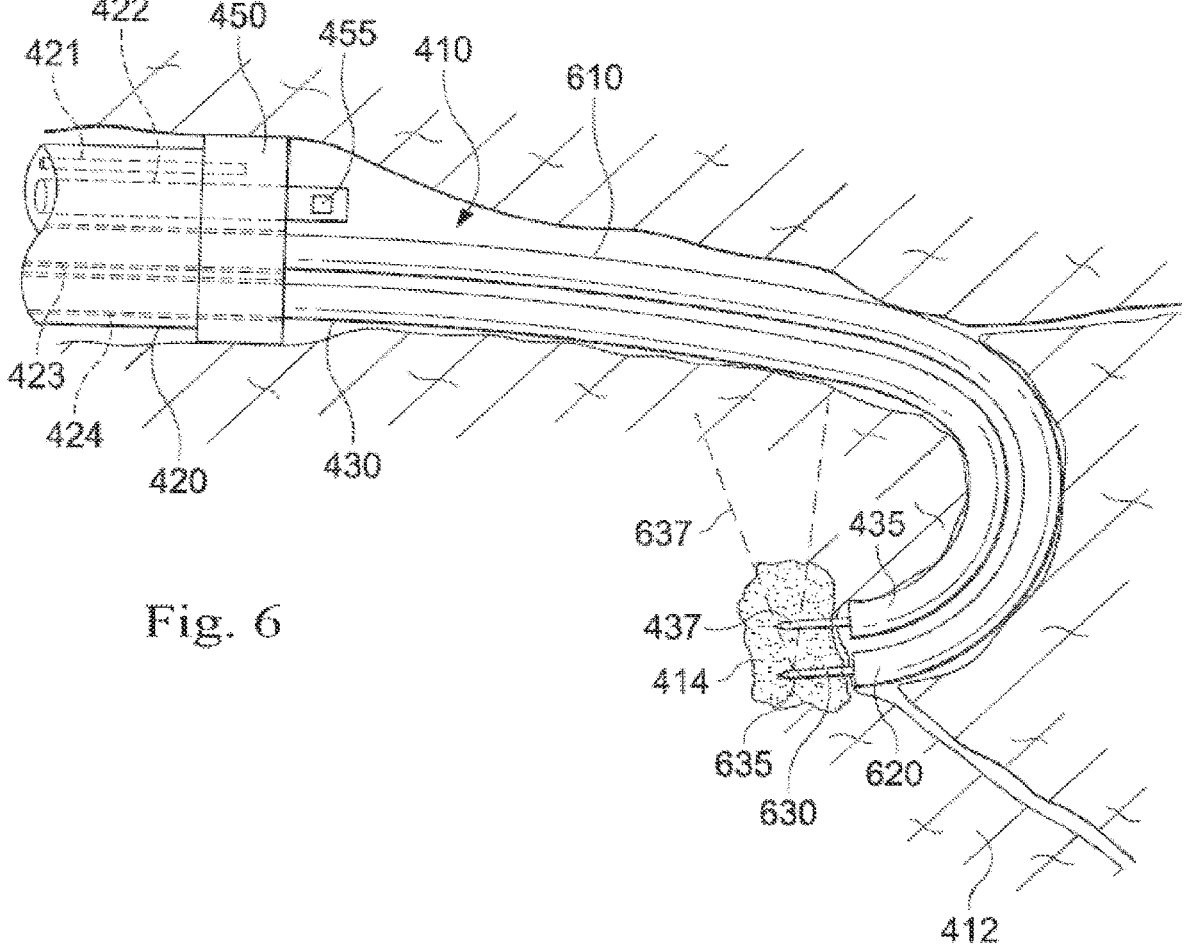
FIG. 6 is a simplified diagram of side views of medical instruments within patient anatomy according to some embodiments.

FIG. 6 is a simplified diagram of side views of medical instruments within patient anatomy according to some embodiments. As shown in FIG. 6, imaging probe 440 of FIGS. 4A and 4B is replaced in favor of an imaging probe 610 equipped with an imaging needle 630. Similar to working catheter 430, imaging probe 610 includes a distal end 620, which may be steered so as to orient distal end 620 toward or slightly to the side of lesion 414. In some examples, a position sensor system (such as position sensor system 220) and/or a shape sensor (such as shape sensor 222) may be used to register imaging probe 610 to one or more pre-operative or intra-operative images and/or models of the patient anatomy to guide the operator in steering distal end 620 toward lesion 414. Imaging probe 610 further includes imaging needle 630, which may be mounted and/or deployed from distal end 620. Imaging needle 630 includes one or more imaging elements 635 usable to capture images of lesion 415, tissue 412, biopsy needle 437, and/or the like. In some examples, the one or more imaging elements are consistent with one or more EBUS transducers that may be rotated within imaging needle 630 to capture images along an imaging field of view 637. In practice, the one or more imaging elements 635 are positioned and oriented so that imaging field of view 637 passes through lesion 414 and is able to capture images of both lesion 414 and biopsy needle 437 as it penetrates lesion 414. Imaging probe 610 is advantageous over imaging probe 440 in that imaging needle 630 is capable of being inserted into tissue 412 and/or lesion 414 allowing for a more options when planning where to place the one or more imaging elements 635 so as to guide placement of biopsy needle 437. In some examples, because imaging needle 630 is inserted within tissue 412 at or near lesion 414, it may be possible to obtain images to support a procedure without having to collapse or fully collapse passageways 410. In some examples, extension of imaging needle 630 may be delayed until distal end 620 is positioned near lesion 414 and passageways 410 are collapsed. In some examples, imaging needle 630 may be surrounded by a sleeve (not shown) so that imaging needle 630 may be rotated after being inserted into tissue 412 without additionally disrupting and/or damaging tissue 412. In some examples, the sleeve may be extended after imaging needle 630 is inserted into tissue 412.

As discussed above and further emphasized here, FIG. 6 is merely an example which should not unduly limit the scope of the claims. One of ordinary skill in the art would recognize many variations, alternatives, and modifications. In some embodiments, imaging probe 610 and imaging needle 630 may optionally be deployed through a lumen within working catheter 430. In some embodiments, biopsy needle 437 may be omitted when imaging needle 630 is further configured to take a tissue sample.

As discussed above and further emphasized here, FIGS. 4A-6 are merely examples which should not unduly limit the scope of the claims. One of ordinary skill in the art would recognize many variations, alternatives, and modifications. In some embodiments, different configurations of the medical instruments are possible. In some examples, biopsy needle 437 may be replaced by other biopsy instruments, ablation devices, cryotherapeutic devices, drug delivery needles, and/or other surgical, diagnostic, or therapeutic tools. In some examples, ultrasound transducers such as side-facing, forward-facing transducers, curved transducers, radial transducers, and/or the like may be used for the one or more imaging elements 445. In some examples, the one or more balloons 450 may be replaced by a series of balloons located at different points along instrument catheter 420 to create a series of seal points within the sealed passageway 410. In some examples, the one or more balloons 450 may include multiple side-by-side balloons that each enlarge to close off a portion of passageway 410 at the seal point. In some examples, the one or more balloons 450 may be mounted on a sleeve around the outside of instrument catheter 420.

In some embodiments, either of working lumen 423 and/or imaging lumen 424 may optionally be omitted and replaced by a combined lumen. When the combined lumen is used, both working catheter 430 and imaging probe 440 may be deployed into passageways 410 via the combined lumen.

In some embodiments, evacuation lumen 422 with evacuation port 455 may be omitted and replaced by other mechanisms to remove air from the passageways. In some examples, one or more open lumens in working catheter 430 and/or imaging probe 440 may include a proximal vacuum which can be used to aid in siphoning of passageways 410 during airway collapse. In some examples, the one or more balloons 450 may optionally include one or more flaps and/or value structures to allow air to be removed distal to the seal point.

In some embodiments, one of the instrument catheter 420, working catheter 430, and imaging probe 440 includes a position sensor system (such as position sensor system 220). The working catheter 430 and imaging probe 440 are received in lumens within the instrument catheter 420 so the relative positions of the instrument catheter 420, working catheter 430, and imaging probe 440 can be determined based on the construction of instrument catheter 420 and known or measured insertion distances (e.g., using sensors or gauges at the proximal end of the devices to measure insertion) of the working catheter 430 and imaging probe 440 relative to the instrument catheter 420.

In some examples, the working catheter 430 may include a position sensor system (such as position sensor system 220) to register the working catheter 430 to one or more pre-operative or intra-operative images and/or models of the patient anatomy. The working catheter 430 may be received and positioned within the working lumen 423 of the instrument catheter with a distal end 435 of the working catheter 430 flush to, near or proximal to a distal end of the instrument catheter 420 prior to insertion of the instrument catheter 420 within passageways 410. The instrument catheter 420 and working catheter 430 can be steered as an assembly to position the distal end of the instrument catheter at the seal point. The position sensor system within the working catheter 430 can provide real time localization of both the working catheter 430 and instrument catheter 420 to help guide the operator in steering the distal end of the instrument catheter.

Instrument catheter 420 can be parked at the seal point at a known location as measured by the position sensor system then working catheter 430 may be inserted beyond the distal end of instrument catheter 420. The position sensor system within working catheter 430 can provide real time localization of working catheter 430 to help guide the operator in steering distal end 435 of working catheter 430 in closer proximity to lesion 414. The position of imaging probe 440 can be determined based on construction of instrument catheter 420 and known or measured insertion distances of imaging probe 440. Thus imaging probe 440 can also be steered through imaging lumen 424 and positioned at a location where it is advantageous for the one or more imaging elements 445 to take intra-operative and real time images of lesion 414. It should be understood that while in this example only working catheter 430 includes a sensor position system 220, position sensor system 220 can be included in working catheter 430, instrument catheter 420, and imaging probe 440 or within any combination of devices while the relative position of a device without a position sensor system may be determined by the construction of instrument catheter 420 and measured/calculated insertion of the device (e.g., using sensors or gauges at the proximal end of the devices).

Figure 7A:
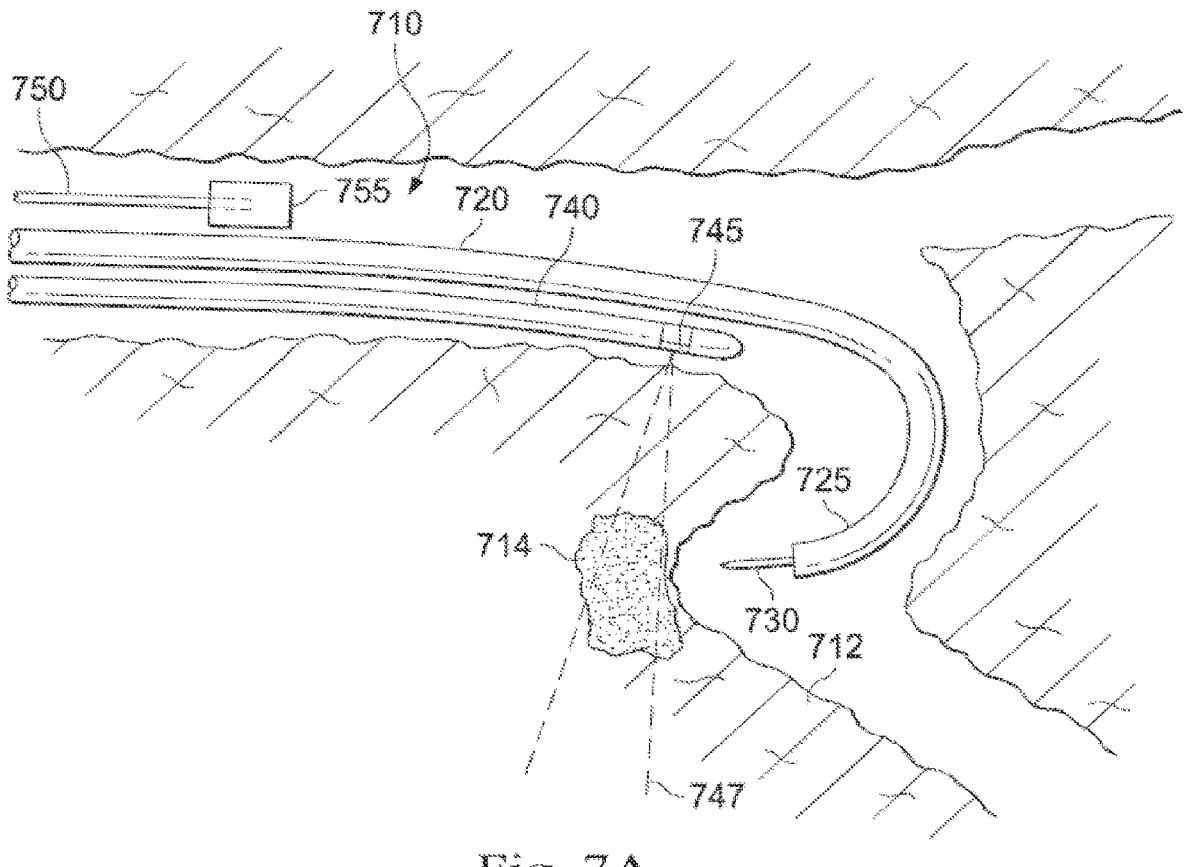
FIGS. 7A and 7B are simplified diagrams of side views of medical instruments within patient anatomy according to some additional embodiments.

In alternate embodiments to FIGS. 4A-6, FIGS. 7A and 7B show simplified diagrams of side views of medical instruments within patient anatomy where instrument catheter 420 is replaced in favor of three separate probes including a flexible catheter 720, an imaging probe 740, and a balloon catheter or sealing probe 750. As shown in FIG. 7A, the patient anatomy includes a plurality of passageways 710 surrounded by tissue 712 prior to collapsing of passageways 710 distal to a seal point within passageways 710 as is described further below. In some examples, passageways 710 may correspond to airways of a patient's lungs. Located within tissue 712 is a region of interest 714, which may correspond to a lesion, a tumor, and/or the like. Thus, region of interest 714 may also be referred to herein as a lesion 714 or a tumor 714. As further shown, passageways 710 are not collapsed, and have inserted into them several medical instruments. In some examples, each of the medical instruments may be consistent with elongate instrument 202.

Flexible catheter 720 includes one or more lumens (not shown) for introducing one or more medical instruments in proximity to lesion 714. Flexible catheter 720 includes a distal end 725, which may be steered so as to orient distal end 725 toward lesion 714. In some examples, a position sensor system (such as position sensor system 220) and/or a shape sensor (such as shape sensor 222) may be used to register flexible catheter 720 to one or more pre-operative or intra-operative images and/or models of the patient anatomy and to provide real time localization of the flexible catheter 720 to help guide the operator in steering distal end 725 toward lesion 714. In some examples, an endoscope inserted through one of the lumens may further be used to aid the operator in positioning and/or orienting distal end 725. A biopsy needle 730 is shown extended beyond distal end 725 to allow a tissue sample to be taken, although in some examples, extension of biopsy needle 730 may be delayed until distal end 725 is properly positioned. In some examples, the endoscope and the biopsy needle 730 may simultaneously be inserted through lumens within catheter 720. Alternatively, the endoscope can be used during navigation through anatomy to the region of interest 714 where the catheter 720 may be parked. The endoscope may then be removed from catheter 720 and replaced with the biopsy needle 730.

Imaging probe 740 includes one or more imaging elements 745 located near its distal end. As shown, imaging probe 740 is located within passageways 710 where it is advantageous for the one or more imaging elements 745 to take intra-operative and real-time images of lesion 714. Similar to flexible catheter 720, a position sensor system and/or a shape sensor may be used to register imaging probe 740 to the one or more pre-operative or intra-operative images to provide real time localization of the imaging probe 740 to help guide the operator in positioning and/or orienting the one or more imaging elements 745 to take images of lesion 714. In some examples, the one or more imaging elements 745 may alternatively or additionally be usable to capture images of flexible catheter 720, imaging probe 740, distal end 725, biopsy needle 730, and/or one or more fiducial markers located on flexible catheter 720 and/or biopsy needle 730 to further aid in registering the images captured by imaging probe 740 and/or localizing imaging probe 740 relative to lesion 714 and/or biopsy needle 730. As shown, the one or more imaging elements 745 are consistent with one or more transducers that may be rotated, by rotating imaging probe 740, to capture images in an imaging field of view 747 directed toward lesion 714. In practice, the one or more imaging elements 745 are positioned and oriented so that imaging field of view 747 passes through lesion 714 and is able to capture images of both lesion 714 and biopsy needle 730 as it penetrates lesion 714. In some embodiments, the one or more imaging elements 745 may be replaced by an array of imaging elements capable of capturing images in all directions around imaging probe 740 without having to rotate the imaging elements in the array.

Sealing probe 750 may be used to create a seal across one of passageways 710, prior to collapsing passageways 710 distal to the seal point. To create the seal, sealing probe 750 includes one or more balloons 755, which may be expanded and/or enlarged to fill the passageway 710 at the seal point and to conform around flexible catheter 720 and/or imaging probe 740. In some examples, air, saline, and/or some other gas or fluid is injected into the one or more balloons 755 through one or more lumens in sealing probe 750 to expand the one or more balloons 755. FIG. 7C is a simplified diagram of a cut-away view of the one or more balloons 755 expanded to fill one of the passageways 710 according to some embodiments. As shown in FIG. 7C, the one or more balloons 755 are expanded until they reach the tissue 712 surrounding the passageway 710 where they are sufficiently malleable to conform to the shape of the tissue 712 at the seal point. Additionally, the one or more balloons 755 are capable of conforming in shape about flexible catheter 720 and imaging probe 740 to effectively seal the passageway 710. FIG. 7D is a simplified diagram of a cross-sectional view of the passageway 710 further showing the conformance in shape of the one or more balloons 755 about the passageway 710 as well as flexible catheter 720 and imaging probe 740. FIG. 7E is a simplified diagram of a cross-sectional view of alternate embodiments of the one or more balloons 755 where flexible catheter 720 and imaging probe 740 are inserted through a port 760 in the one or more balloons 755. In some examples, port 760 may optionally include one or more flaps and/or value structures to support sealing around flexible catheter 720 and/or imaging probe 740 when the one or more balloons 755 are expanded.

Figure 7B:
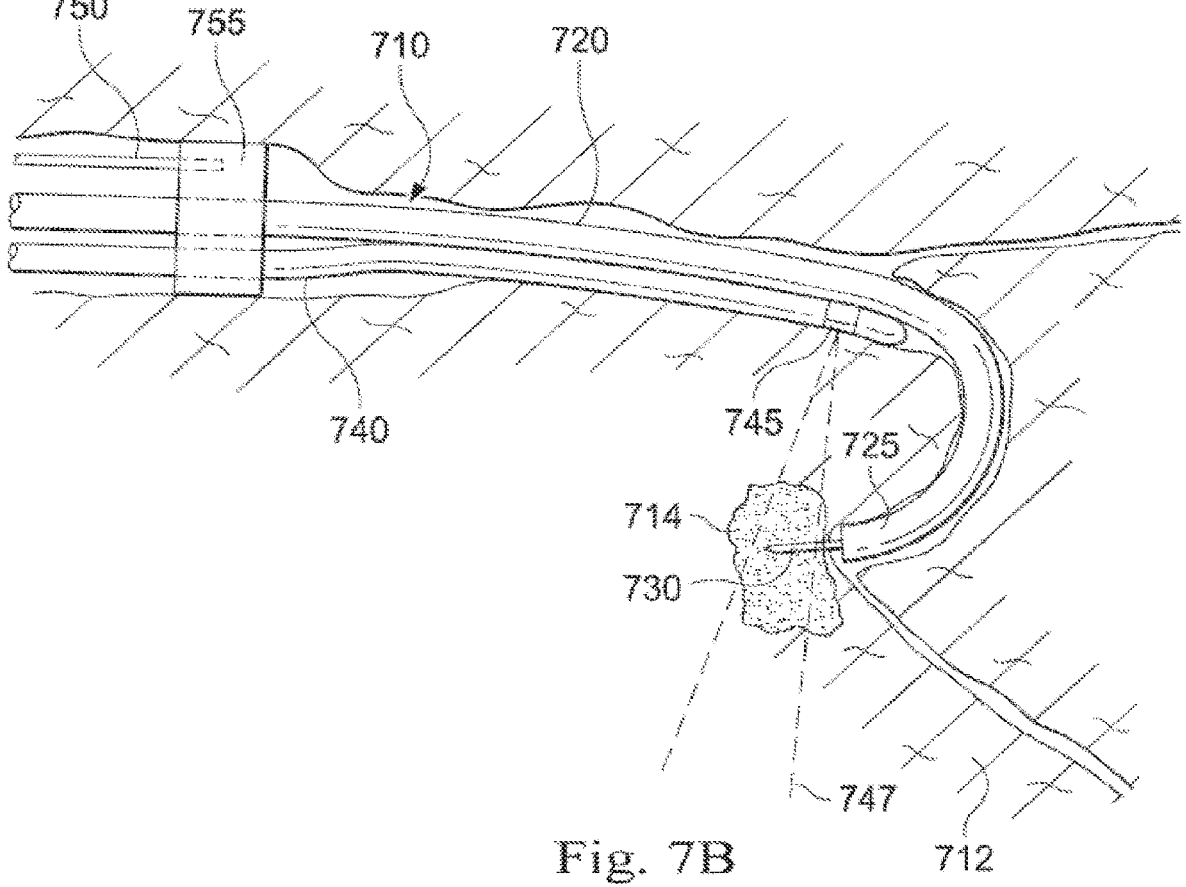

Once passageway 710 is sealed, the passageways 710 distal to the seal point are allowed to collapse about flexible catheter 720 and imaging probe 740 as shown in FIG. 7B. In some examples, the air within passageways 710 is removed by operating one or more flaps or valves (not shown) in the one or more balloons 755 and/or by siphoning the air out of passageways 710 through a lumen in flexible catheter 720, imaging probe 740, and/or sealing probe 750.

As discussed above and further emphasized here, FIGS. 7A-7E are merely examples which should not unduly limit the scope of the claims. One of ordinary skill in the art would recognize many variations, alternatives, and modifications. In some embodiments, different configurations of the medical instruments are possible. In some examples, biopsy needle 730 may be replaced by other biopsy instruments, ablation devices, cryotherapeutic devices, drug delivery needles, and/or other surgical, diagnostic, or therapeutic tools. In some examples, ultrasound transducers such as side-facing, forward-facing transducers, curved transducers, radial transducers, and/or the like may be used for the one or more imaging elements 745. In some examples, the one or more balloons 755 may be replaced by a series of balloons located at different points along sealing probe 750 to create a series of seal points within the sealed passageway 710. In some examples, the one or more balloons 755 may include multiple side-by-side balloons that each enlarge to close off a portion of passageway 710 at the seal point.

In some embodiments, imaging probe 740 may be inserted into different passageways 710 than flexible catheter 720 in much the same manner as shown in the embodiments of FIG. 5. As long as the one or more imaging elements 745 are within range of lesion 714, are positionable and orientable to capture images of lesion 714, and are located distal to the one or more balloons 755 any combination of passageways may be used.

In some embodiments, the structures and/or functionalities of flexible catheter 720, imaging probe 740, and/or sealing probe 750 may be combined so that they are deployable in the passageways using two or fewer elongate instrument bodies. In some examples, imaging probe 740 and the one or more imaging elements 745 may be deployed within a lumen within flexible catheter 720 and then extended and/or retracted within the lumen to position and orient the one or more imaging elements 745 relative to lesion 714. In some examples, imaging probe 740 and the one or more imaging elements 745 may be inserted through a lumen of flexible catheter 720 that has a side port located somewhere along the elongated body of flexible catheter 720, thus allowing the one or more imaging elements 745 to be deployed outside of flexible catheter. In some examples, an imaging transducer may be integrated onto the exterior of flexible catheter 720. In some examples sealing probe 750 may similarly be inserted through a lumen of flexible catheter 720 that has a side port located along somewhere along the elongated body of flexible catheter 720 allowing the one or more balloons 755 to be deployed outside flexible catheter 720. In some examples, a separate sealing probe 750 is omitted and the one or more balloons 755 may be mounted to the exterior of flexible catheter 720 and/or imaging probe 740 with one or more lumens provided in flexible catheter 720 and/or imaging probe 740 to provide the gas or fluid used to expand the one or more balloons 755. In some examples, the one or more balloons 755 and the one or more gas or fluid lumens may be mounted on a sheath that surrounds flexible catheter 720 and/or imaging probe 740. In some examples, flexible catheter 720 carries a biopsy needle with an open lumen. The open lumen may include a proximal vacuum which can be used to aid in siphoning of passageways 710 during airway collapse.

In some examples, an adaptor (such as adaptor 320 having insertion channels 331-333 for accepting medical instruments) may be used to insert the instrument catheter 720, biopsy needle 730, and/or imaging probe 740 into one or more passageways, such as the airways of lungs of a patient. With known construction of adaptor 320 and relative known positions of insertion channels 331-333, the relative radial positions of instrument catheter 720, biopsy needle 730, and/or imaging probe 740 could be determined relative to one another. Relative insertion of each of instrument catheter 720, biopsy needle 730, and/or imaging probe 740 could be measured/calculated using sensors or gauges at the proximal end of the instruments. A position sensor system (such as position sensor system 220) can be included within any one of the devices such as biopsy needle 730, instrument catheter 720, imaging probe 740, or within any combination of the three devices giving the position, orientation, and/or pose of the device in a fixed coordinate system (such as a patient coordinate system). With known relative position of devices to one another based on adaptor 320 and measured/calculated insertions, the position of biopsy needle 730, instrument catheter 720, and/or imaging probe 740 can each be determined.

FIG. 8 is a simplified diagram of a method 800 of performing a procedure using integrated real-time imaging according to some embodiments. One or more of the processes 805-870 of method 800 may be implemented, at least in part, in the form of executable code stored on nontransient, tangible, machine readable media that when run by one or more processors (e.g., one or more processors of control system 112) may cause the one or more processors to perform one or more of the processes 805-875. In some embodiments, method 800 is usable to manipulate one or more medical instruments, such as any of the instruments discussed above with respect to FIGS. 2, and/or 4A-6, to perform a procedure where integrated real-time imaging of target anatomy, such as lesion 414 is desirable. The ordering of processes 805-870 in FIG. 8 is exemplary only and other possible orderings and/or arrangements of processes 805-870 are possible. In some examples, one or more of processes 805-870 may be performed concurrently. In some examples, processes 855-865 may be performed concurrently so that real-time images obtained by the imaging probe may be continuously obtained to locate the target anatomy and to monitor whether a medical tool is properly deployed to the target anatomy. In some embodiments, other processes not shown in FIG. 8 may also be part of method 800.

At a process 805, one or more pre-operative images are obtained of a target anatomy. Using any suitable imaging technology, such as CT, MRI, fluoroscopy, thermography, ultrasound, OCT, thermal imaging, impedance imaging, laser imaging, nanotube X-ray imaging, and/or the like, image data is obtained. This pre-operative image data is processed to generate one or more two-dimensional, three-dimensional, or four-dimensional (including e.g., time based or velocity based information) images. In some examples, the images may further be processed to create one or models of the target anatomy, including locations and orientations of passageways usable to reach the target anatomy. In some examples, the target anatomy may correspond to a tumor or lesion, such as lesion 414. In some examples, the one or more images and/or one or more models may further account for a phase of anatomic motion (e.g., respiration, heart activity, and/or the like) in order to better model changes within the target anatomy and/or the passageways due to the anatomic motion.

At a process 810, a procedure is planned using the one or more images and/or the one or more models obtained during process 805. Elements of the plan include determining paths through the passageways for each of the medical instruments including, for example, instrument catheter 420, imaging probe 440 and/or 610, and/or working catheter 430. Additional elements of the plan include determining target locations for positioning and orienting each of the medical instruments for its intended task. In some examples, this includes determining where to position and orient the distal end of a working catheter, such as distal end 435 of working catheter 430, so that a medical tool, such as biopsy needle 437, can be deployed for use on the target anatomy. This further includes determining where to position and orient the one or more imaging elements, such as the one or more imaging elements 445 of imaging probe 440 and/or the one or more imaging elements 635 of imaging needle 630, so that an imaging field of view, such as imaging field of view 447 and/or 637, is able to capture real-time intraoperative images of the target anatomy as well as the medical tool being deployed using the working catheter. In some examples, a desired imaging field of view includes an image of the working catheter. Alternatively, the desired imaging field of view is obtained by positioning the imaging probe directly adjacent a passageway wall containing the target anatomy. Elements of the plan can additionally include determining where to position and orient one or more sealing balloons, such as the one or more balloons 450, so that the passageways contain the one or more imaging elements and the distal end of the working catheter, such as working catheter 430, may be collapsed as desired during the procedure.

At a process 815, the instrument catheter is inserted into the passageways. Using, for example, adaptor 320 and/or ET tube 310, the instrument catheter is inserted into one or more passageways, such as the airways of the lungs of patient P (corresponding to passageways 410). In some examples, navigation of the instrument catheter within the passageways may be aided by an imaging device, such as an endoscope, providing images from the distal end of the instrument catheter.

At a process 820, the instrument catheter is registered to the preoperative images and/or models obtained during process 805. As the instrument catheter is inserted into and moved around the passageways, position and orientation for the instrument catheter and the distal end of the instrument catheter are gathered using, for example, shape sensor 222 and/or position sensor system 220. As this position and orientation data is collected, it is correlated with the similar position and orientation data on the passageways determined using the one or more models obtained during process 805. Once sufficient position and orientation data for the instrument catheter and/or the distal end are obtained, a registration transform is developed that maps position and orientation data obtained for the instrument catheter and the distal end into the models obtained during process 805. This registration transform is typically suitable to address position, scaling, and/or orientation differences between the actual patient anatomy navigated by the working catheter and the distal end and the model data for the same patient anatomy obtained during process 805. For example U.S. patent application Ser. No. 13/107,562 (filed May 13, 2011) (disclosing "Medical System Providing Dynamic Registration of a Model of an Anatomic Structure for Image-Guided Surgery") which is incorporated by reference herein in its entirety discloses several approaches for performing such a registration. In some examples, the shape sensor and/or the position detection system may further be used to develop a kinematic model that tracks the position and orientation of the distal end relative to a proximal end of the instrument catheter. In some examples, the proximal end may correspond to a known point on adaptor 320 and/or a point associated with an actuator used to insert and/or retract the instrument catheter within the passageways.

At a process 825, the instrument catheter is driven to a seal point using the one or more plans determined during process 810 and the registration of process 820. As the instrument catheter is driven, additional position and orientation data obtained using the shape sensor and/or position sensing system may be used to continually monitor the position and orientation of the distal end of the instrument catheter relative to the passageways and the target anatomy. In some examples, navigation of the instrument catheter within the passageways may be aided by an imaging device, such as an endoscope, providing images from the distal end of the instrument catheter. In some examples, information from the one or more plans obtained during process 810 may be used to provide guidance to the operator using haptic feedback and/or a display system, such as display system 110, by providing directional hints, virtual overlays, and/or the like.

At a process 830, the instrument catheter is oriented and then parked. When the distal end of the instrument catheter is positioned at the seal point determined during the planning of process 810, the distal end of the instrument catheter is oriented to align the distal end of the instrument catheter with the passageways at the seal point. As the instrument catheter is oriented, additional position and orientation data obtained using the shape sensor and/or position sensing system may be used to continually monitor the position and orientation of the instrument catheter relative to passageways and the target anatomy. In some examples, position and orientation data using the shape sensing and/or positioning sensing of the working catheter can be used in place of or in addition to known relative positions of the working catheter in relation to the imaging probe. In some examples, the instrument catheter may be further rotated based on the cross-sectional shape of the passageways at the seal point to align one or more pre-shaped balloons with the cross-sectional shape. In some examples, the instrument catheter can additionally or alternatively be rotated in order to provide positioning of the imaging probe as it exits the distal end of the instrument catheter to an orientation in relation the target anatomy which achieves the desired imaging field of view. Once the instrument catheter is oriented, it is parked. The parking positions the instrument catheter within the passageways so that it is not further inserted and/or retracted within the passageways. In some examples, a stiffness of the instrument catheter may further be increased so that the instrument catheter is further held in position within the passageways.

At a process 835, an imaging probe, such as imaging probe 440 and/or imaging probe 610, is inserted into the passageways through a lumen, such as imaging lumen 424, within the instrument catheter and then driven toward the imaging position. In some examples, imaging probe may be inserted into the lumen of the instrument catheter before process 815 and then extended beyond the distal end of the instrument catheter during process 835. Using processes similar to processes 815-830, the imaging probe is inserted into the passageways, registered to the one or more models obtained during process 805, and driven toward the imaging position according to the plan determined during process 810. In some examples, information from the one or more plans obtained during process 810 may be used to provide guidance to the operator using haptic feedback and/or a display system, such as display system 110, by providing directional hints, virtual overlays, and/or the like. Registration of the imaging probe can be obtained using position and orientation information obtained by the shape sensor 222 and/or position sensor system 220 integrated within the imaging probe. Alternatively, imaging probe position and orientation can be known relative to a fixed relative position to the instrument catheter based on instrument catheter construction and/or relative position of the imaging probe to the working catheter. For example, the imaging probe will be received within a lumen within the instrument catheter and the relative position of the lumen will be known based on the construction of the catheter. The insertion of the imaging probe can be determined based on sensors and/or gauges at a proximal end of the imaging probe. In some examples, insertion of the imaging probe can be determined using images from the endoscope providing images from the distal end of the instrument.

The imaging probe and the one or more imaging elements are further oriented so that an imaging field of view, such as imaging field of view 447 and/or 637, is likely to be able to obtain images of the target anatomy and the medical tool deployed using a working catheter. In some examples, the one or more imaging elements may also be localized relative to the target anatomy and/or the distal end of the instrument catheter and/or the distal end of the working catheter. Localizing the one or more imaging elements to the target anatomy and/or the distal end of the instrument catheter allows positions of the target anatomy, the distal end of the instrument catheter, and/or the medical tool deployed at the distal end of the working catheter observed within the images obtained by the one or more imaging elements to be more easily mapped to movements and/or adjustments to the distal end of the working catheter and/or the medical tool so that the medical tool may be deployed within the target anatomy. In some examples, the localizing may be Obtained by combining the registration transform of the instrument catheter and/or the working catheter with the registration transform of the imaging probe through a common reference point, such as a point on adaptor 320. In some examples, the localizing may further include continued monitoring of the positions and orientations of the working catheter and/or the imaging probe using respective shape sensors and/or position sensor systems and/or localization information obtainable using images of the working catheter, the distal end of the working catheter, and/or the medical tool obtained using the one or more imaging elements. In some examples, one or more fiducial markers, such as emitters and/or special markers, mounted to known locations on the working catheter, the distal end of the working catheter, and/or the medical tool may also contribute to the localization.

At a process 840, the working catheter, such as working catheter 430, is inserted into the passageways through a lumen, such as working lumen 423, within the instrument catheter and then driven toward the target anatomy according to the plan determined in process 810. In some examples, information from the one or more plans obtained during process 810 may be used to provide guidance to the operator using haptic feedback and/or a display system, such as display system 110, by providing directional hints, virtual overlays, and/or the like. In some examples, working catheter may be inserted into the lumen of the instrument catheter before process 815 and then extended beyond the distal end of the instrument catheter during process 840. Using processes similar to processes 815-830 and/or 835, the working catheter is inserted into the passageways, registered to the one or more models obtained during process 805, and driven toward the target anatomy. In some examples, movement of the distal end of the working catheter may be further guided using an endoscope inserted through a lumen in the working catheter. In some examples, the distal end of the working catheter may also be localized relative to the target anatomy and/or the imaging probe. In some examples, the localizing may be obtained by combining the registration transform of the instrument catheter and/or the instrument probe with the registration transform of the working catheter through a common reference point, such as a point on adaptor 320. In some examples, the localizing may further include continued monitoring of the positions and orientations of the working catheter and/or the imaging probe using respective shape sensors and/or position sensor systems and/or localization information obtainable using images of the working catheter, the distal end of the working catheter, and/or the medical tool obtained using the one or more imaging elements of the imaging probe. In some examples, one or more fiducial markers, such as emitters and/or special markers, mounted to known locations on the working catheter, the distal end of the working catheter, and/or the medical tool may also contribute to the localization.

At a process 845, the passageway is closed at the seal point by enlarging the one or more sealing balloons located at the distal end of the instrument catheter. The one or more balloons may be enlarged by injecting air, saline, and/or some other gas or fluid into the one or more sealing balloons using one or more lumens, such as inflation lumen 421 within the instrument catheter so that the one or more sealing balloons fill the passageway at the seal point, and conform to the shape of the passageway at the seal point.

At a process 850, one or more passageways distal to the seal point are collapsed. In some examples, air within the one or more passageways distal to the seal point is removed by vacuuming or siphoning it through an evacuation port, such as evacuation, port 455 of evacuation lumen 422. In some examples, the air within the one or more passageways may optionally be siphoned from the one or more passageways using one or more lumens in the sealing probe, the imaging, probe, the working catheter, and/or a device carried within the working catheter such as a biopsy needle with an open lumen.

At a process 855, the imaging probe is adjusted to obtain images of the target anatomy. Because the positioning and/or orienting of the one or more imaging elements during process 835 may be inaccurate and/or the positioning and/or orienting may be disturbed as the one or more passageways distal to the seal point are collapsed, the imaging probe and the one or more imaging elements may be adjusted to align the imaging field of view with the target anatomy. In some examples, the images are obtained and used to aid in adjustment of the imaging probe such that the imaging probe is inserted or retracted in the passageways and rotated until the target anatomy is in view. In some examples, position and/or orientation data from the shape sensor or position sensor system may be used to aid the adjustment of the imaging probe. In some examples, guidance for adjusting the imaging probe, such as haptic feedback and/or direction hints, virtual overlays, and/or the like, may be provided to the operator using a display system, such as display system 110.

At a process 860, an image is obtained using the one or more imaging elements of the imaging probe. In some examples, when the one or more imaging elements include one or more transducers, the image may be obtained by rotating the imaging probe to obtain a planar slice around the imaging probe that is aligned with an imaging field of view, such as imaging field of view 447 and/or 637, and/or oriented with the target anatomy. The obtained image is then analyzed to determine a location of the target anatomy relative to the imaging probe.

At a process 865, the medical tool is driven to the target anatomy by adjusting the working catheter and/or by deploying the medical tool relative to the distal end of the working catheter. In some examples, the image obtained during process 860 along with the localization determined during processes 835 and/or 840 may be used to adjust the position of the working catheter and/or the distal end of the working catheter relative to the target anatomy. In some examples, when the medical tool is biopsy needle 437, biopsy needle 437 may be driven by extending it into the target anatomy where it may be captured within the image obtained during process 860. In some examples, the medical tool may be consistent with other biopsy instruments, ablation devices, cryotherapeutic devices, drug delivery needles, and/or other surgical, diagnostic, or therapeutic tools. In some examples, when the image obtained during process 860 does not include the target anatomy, process 860 may be omitted until a real-time image of the target anatomy is Obtained by the imaging probe. Processes 855-865 may then be repeated to continually adjust the imaging probe, obtain images, and drive the medical tool so as to provide real-time monitoring of the procedure being performed using the medical tool.

At a process 870, the one or more passageways collapsed during process 850 are re-inflated. In some examples, the one or more passageways may be re-inflated by deflating the one or more balloons by opening the one or more flaps and/or the one or more valves located on the one or more balloons and allowing the passageways to re-inflate naturally as the patient is breathing. In some examples, the one or more passageways may be re-inflated by re-introducing air or another suitable gas into the one or more passageways using the one or more lumens in the working catheter, the imaging probe, and/or the sealing probe used to collapse the one or more passageways during process 850.

In some examples, when processes 855-865 are not able to complete the procedure, process 870 may include partially re-inflating the one or more passageways so that the imaging probe and/or the working catheter may be repositioned and/or reoriented (e.g., by performing processes 855 and/or 865 while the one or more passageways are partially re-inflated) before re-collapsing the one or more passageways by returning to process 850. In some examples, the partial re-inflation of the one or more passageways allows for more movement in the imaging probe and/or the working catheter because the partially collapsed one or more passageways do not impede movement of the imaging probe and/or the working catheter as much as the fully collapsed one or more passageways.

Figure 9:
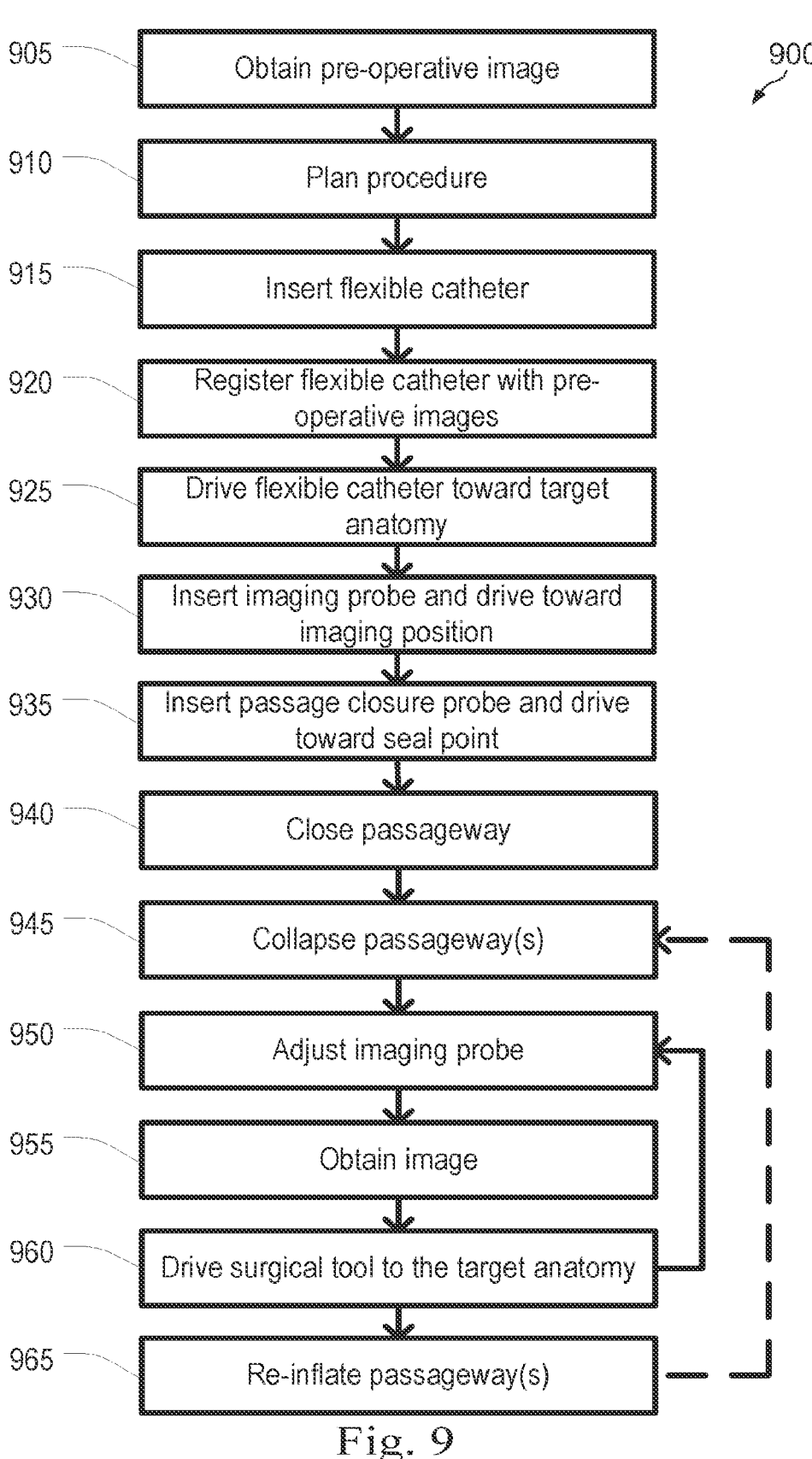
FIG. 9 is a simplified diagram of a method of performing a procedure using integrated real-time imaging according to some additional embodiments.

FIG. 9 is a simplified diagram of a method 900 of performing a procedure using integrated real-time imaging according to some additional embodiments. One or more of the processes 905-965 of method 900 may be implemented, at least in part, in the form of executable code stored on non-transient, tangible, machine readable media that when run by one or more processors (e.g., one or more processors of control system 112) may cause the one or more processors to perform one or more of the processes 905-965. In some embodiments, method 900 is usable to manipulate one or more medical instruments, such as any of the instruments discussed above with respect to FIGS. 2 and/or 7A-7E, to perform a procedure where integrated real-time imaging of target anatomy, such as lesion 714 is desirable. The ordering of processes 905-965 in FIG. 9 is exemplary only and other possible orderings and/or arrangements of processes 905-965 are possible. In some examples, processes 920-735 may be performed in other orders and/or any two or more may be performed concurrently. In some embodiments, process 935 may be performed prior to processes 915-930 so that a flexible catheter and/or a.n imaging probe may be inserted through one or more ports, such as port 760 after one or more balloons used for sealing are deployed within the passageways. In some examples, processes 950-960 may be performed concurrently so that real-time images obtained by the imaging probe may be continuously obtained to locate the target anatomy and to monitor whether a medical tool is properly deployed to the target anatomy. In some embodiments, other processes not shown in FIG. 9 may also be part of method 900.

At a process 905, one or more pre-operative images are obtained of a target anatomy. Using any suitable imaging technology, such as CT, MRI, fluoroscopy, thermography, ultrasound, OCT, thermal imaging, impedance imaging, laser imaging nanotube X-ray imaging, and/or the like, image data is obtained. This pre-operative image data is processed to generate one or more two-dimensional, three-dimensional, or four-dimensional (including e.g., time based or velocity based information) images. In some examples, the images may further be processed to create one or models of the target anatomy, including locations and orientations of passageways usable to reach the target anatomy. In some examples, the target anatomy may correspond to a tumor or lesion, such as lesion 414. In some examples, the one or more images and/or one or more models may further account for a phase of anatomic motion (e.g., respiration, heart activity, and/or the like) in order to better model changes within the target anatomy and/or the passageways due to the anatomic motion.

At a process 910, a procedure is planned using the one or more images and/or the one or more models obtained during process 905. Elements of the plan include determining paths through the passageways for each of the medical instruments including, for example, flexible catheter 720, imaging probe 740, and/or sealing probe 750. Additional elements of the plan include determining target locations for positioning and orienting each of the medical instruments for its intended task. In some examples, this includes determining where to position and orient the distal end of a flexible catheter, such as distal end 725 of flexible catheter 720, so that a medical tool, such as biopsy needle 730, can be deployed for use on the target anatomy. This further includes determining where to position and orient the one or more imaging elements, such as the one or more imaging elements 745 of imaging probe 740 and/or the one or more imaging elements 635 of imaging needle 630, so that an imaging field of view, such as imaging field of view 447 and/or 637, is able to capture real-time intraoperative images of the target anatomy as well as the medical tool being deployed using the flexible catheter. In some examples, a desired imaging field of view includes an image of the flexible catheter. Alternatively, the desired imaging field of view is obtained by positioning the imaging probe directly adjacent a passageway wall containing the target anatomy. Elements of the plan can additionally include determining where to position and orient one or more sealing balloons, such as the one or more balloons 755 of sealing probe 750, so that the passageways contain the one or more imaging elements and the distal end of the flexible catheter, such as flexible catheter 420, may be collapsed as desired during the procedure.

At a process 915, the flexible catheter is inserted into the passageways. Using, for example, adaptor 320 and/or ET tube 310, the flexible catheter is inserted into one or more passageways, such as the airways of the lungs of patient P (corresponding to passageways 710), and is navigated by the operator. In some examples, navigation of the flexible catheter within the passageways may be aided by an imaging device, such as an endoscope, providing images from the distal end.

At a process 920, the flexible catheter is registered to the preoperative images and/or models obtained during process 905. As the flexible catheter is inserted into and moved around the passageways, position and orientation for the flexible catheter and the distal end are gathered using, for example, shape sensor 222 and/or position sensor system 220. As this position and orientation data is collected, it is correlated with the similar position and orientation data on the passageways determined using the one or more models obtained during process 905. Once sufficient position and orientation data for the flexible catheter and/or the distal end are obtained, a registration transform is developed that maps position and orientation data obtained for the flexible catheter and the distal end into the models obtained during process 905. This registration transform is typically suitable to address position, scaling, and/or orientation differences between the actual patient anatomy navigated by the flexible catheter and the distal end and the model data for the same patient anatomy obtained during process 905. For example U.S. patent application Ser. No. 13/107,562 (filed May 13, 2011) (disclosing "Medical System Providing Dynamic Registration of a Model of an Anatomic Structure for Image-Guided Surgery") which is incorporated by reference herein in its entirety, discloses several approaches for performing such a registration. In some examples, the shape sensor and/or the position detection system may further be used to develop a kinematic model that tracks the position and orientation of the distal end relative to a proximal end of the flexible catheter. In some examples, the proximal end may correspond to a known point on adaptor 320 and/or a point associated with an actuator used to insert and/or retract the flexible catheter within the passageways.

At a process 925, the flexible catheter is driven toward the target anatomy using the one or more plans determined during process 910 and the registration of process 920. As the flexible catheter is driven, additional position and orientation data obtained using the shape sensor and/or position sensing system may be used to continually monitor the position and orientation of the distal end of the flexible catheter relative to the passageways and the target anatomy. In some examples, navigation of the flexible catheter within the passageways may be aided by an imaging device, such as an endoscope, providing images from the distal end of the flexible catheter. When the distal end of the flexible catheter is positioned sufficiently near and oriented toward the target anatomy, a medical tool, such as biopsy needle 730, may be used to access the target anatomy. In some examples, information from the one or more plans obtained during process 910 may be used to provide guidance to the operator using haptic feedback and/or a display system, such as display system 110, by providing directional hints, virtual overlays, and/or the like.

At a process 930, an imaging probe, such as imaging probe 740 and/or imaging probe 610, is inserted and driven toward the imaging position. Using processes similar to processes 915-925, the imaging probe is inserted into the passageways, registered to the one or more models obtained during process 905, and driven toward the imaging point using the one or more plans determined during process 910. The imaging probe and the one or more imaging elements are further oriented so that an imaging field of view, such as imaging field of view 747 and/or 637, is likely to be able to obtain images of the target anatomy and the medical tool deployed using the flexible catheter. In some examples, the one or more imaging elements may also be localized relative to the target anatomy and/or the distal end of the flexible catheter. Localization of the imaging probe can be obtained using position and orientation information obtained by the shape sensor and/or position sensor system integrated within the imaging probe. Alternatively, imaging probe position and orientation can be known relative to a position on the flexible catheter based on flexible catheter and/or imaging probe construction and/or relative position of the imaging probe to the flexible catheter. Localizing the one or more imaging elements to the target anatomy and/or the distal end of the flexible catheter allows positions of the target anatomy, the distal end of the flexible catheter, and/or the medical tool deployed at the distal end of the flexible catheter observed within the images obtained by the one or more imaging elements to be more easily mapped to movements and/or adjustments to the distal end of the flexible catheter and/or the medical tool so that the medical tool may be deployed within the target anatomy. In some examples, the localizing may be obtained by combining the registration transform of the flexible catheter with the registration transform of the imaging probe through a common reference point, such as a point on adaptor 320. In some examples, the localizing may further include continued monitoring of the positions and orientations of the flexible catheter and/or the imaging probe using respective shape sensors and/or position sensor systems and/or localization information obtainable using images of the flexible catheter, the distal end of the flexible catheter, and/or the medical tool obtained using the one or more imaging elements. In some examples, one or more fiducial markers, such as emitters and/or special markers, mounted to known locations on the flexible catheter, the distal end of the flexible catheter, and/or the medical tool may also contribute to the localization.

At a process 935, a sealing probe, such as sealing probe 750, is inserted and driven toward a seal point within passageways 710. Using processes similar to processes 915-725, the sealing probe is inserted into the passageways, registered to the one or more models obtained during process 905, and driven toward the seal point using the one or more plans determined during process 910. In some examples, process 935 may further including positioning one or more sealing balloons, such as the one or more sealing balloons 755, within the passageways at the seal point and/or a plurality of seal points. In some examples, the seal point can be determined as a point proximate the target location which provides for collapse of the passageways which lead to the target location but minimizes the collapse of passageway's not associated with the target location.

At a process 940, the passageway is closed at the seal point by enlarging the one or more sealing balloons of the sealing probe. The one or more balloons may be enlarged by injecting air, saline, and/or some other gas or fluid into the one or more sealing balloons using one or more lumens within the sealing probe so that the one or more sealing balloons fill the passageway at the seal point, conform to the shape of the passageway, and conform to the shape of the flexible catheter and the imaging probe within the passageway at the seal point.

At a process 945, one or more passageways distal to the seal point are collapsed. In some examples, air within the one or more passageways is removed through evacuation lumens including one or one or more flaps, one way valves, and/or the like within the one or more balloons used to seal the passageway during process 940. In some examples, air within the one or more passageways is siphoned from the one or more passageways using one or more lumens in the sealing probe, the imaging, probe, the flexible catheter, and/or a device carried within the flexible catheter such as a biopsy needle with an open lumen.

At a process 950, the imaging probe is adjusted to obtain images of the target anatomy. In some examples, the images are obtained and used to aid in adjustment of the imaging probe such that the imaging probe is inserted or retracted in the passageways and rotated until the target anatomy is in view. Because the positioning and/or orienting of the one or more imaging elements during process 930 may be inaccurate and/or the positioning and/or orienting, may be disturbed as the one or more passageways distal to the seal point are collapsed, the imaging probe and the one or more imaging elements may be adjusted to align the imaging field of view with the target anatomy. In some examples, position and/or orientation data from the shape sensor or position sensor system may he used to aid the adjustment of the imaging probe. In some examples, guidance for adjusting the imaging probe, such as haptic feedback and/or direction hints, virtual overlays, and/or the like, may be provided to the operator using a display system, such as display system 110.

At a process 955, an image is obtained using the one or more imaging elements of the imaging probe. In some examples, when the one or more imaging elements include one or more transducers, the image may be obtained by rotating the imaging probe to obtain a planar slice around the imaging probe that is aligned with an imaging field of view, such as imaging field of view 747 and/or 637, and/or oriented with the target anatomy. The obtained image is then analyzed to determine a location of the target anatomy relative to the imaging probe.

At a process 960, the medical tool is driven to the target anatomy by adjusting the flexible catheter and/or by deploying the medical tool relative to the distal end of the flexible catheter. In some examples, the image obtained during process 955 along with the localization determined during process 930 may be used to adjust the position of the flexible catheter and/or the distal end of the flexible catheter relative to the target anatomy. In some examples, when the medical tool is biopsy needle 730, biopsy needle 730 may be driven by extending it into the target anatomy where it may be captured within the image obtained during process 955. Alternatively, the medical tool may be consistent with other biopsy instruments, ablation devices, cryotherapeutic devices, drug delivery needles, and/or other surgical, diagnostic, or therapeutic tools. In some examples, when the image obtained during process 960 does not include the target anatomy, process 960 may be omitted until a real-time image of the target anatomy is obtained by the imaging probe. Processes 950-760 may then be repeated to continually adjust the imaging probe, obtain images, and drive the medical tool so as to provide real-time monitoring of the procedure being performed using the medical tool.

At a process 965, the one or more passageways collapsed during process 945 are re-inflated. In some examples, the one or more passageways may be re-inflated by deflating the one or more balloons by opening the one or more flaps and/or the one or more valves located on the one or more balloons used to close the passageway. In some examples, the one or more passageways may be re-inflated by reintroducing air or another suitable gas into the one or more passageways using the one or more lumens in the flexible catheter, the imaging probe, and/or the sealing probe used to collapse the one or more passageways during process 945. In some examples, when processes 950-760 are not able to complete the procedure, process 965 may include partially re-inflating the one or more passageways so that the imaging probe and/or the flexible catheter may be repositioned and/or reoriented (e.g., by performing processes 950 and/or 960 while the one or more passageways are partially re-inflated) before re-collapsing the one or more passageways by returning to process 945. In some examples, the partial re-inflation of the one or more passageways allows for more movement in the imaging probe and/or the flexible catheter because the partially collapsed one or more passageways do not impede movement of the imaging probe and/or the flexible catheter as much as the fully collapsed one or more passageways.

EXAMPLES

1. A method of controlling a medical system, the method comprising:
   inserting a flexible catheter, a working catheter, and an imaging probe into anatomic passageways of a patient, wherein the flexible catheter comprises a sealing device;
   driving a distal portion of the flexible catheter towards a target anatomy to a first location, wherein the flexible catheter comprises a sealing device;
   driving a distal portion of the working catheter with guidance from a first positioning system towards the target anatomy to a second location where one or more medical instruments deployed through one or more lumens of the working catheter have access to the target anatomy;
   driving a distal portion of the imaging probe towards the target anatomy to a third location where one or more imaging elements of the imaging probe are able to obtain images of the target anatomy;
   sealing one of the anatomic passageways at the first location using the sealing device, wherein the first location is proximal to the second location and the third location; collapsing the anatomic passageways distal to the sealing device;
   obtaining one or more images of the target anatomy using the imaging probe; and
   performing a procedure on the target anatomy using the one or more medical instruments under guidance from the one or more images.
2. The method of example 1, further comprising adjusting at least one of a position and an orientation of the imaging probe while the anatomic passageways are collapsed.
3. The method of example 1 or 2, further comprising adjusting at least one of a position and an orientation of the working catheter while the anatomic passageways are collapsed.
4. The method of any one of examples 1-3, further comprising partially re-inflating the collapsed anatomic passageways to allow adjustment of at least one of a position and an orientation of at least one of the flexible catheter and the imaging probe.
5. The method of any one of examples 1-4, wherein the second location is in a different branch of the anatomic passageways than the third location.
6. The method of any one of examples 1-5 wherein the first location is in a first branch, the second location is in a second branch, and the third location is in a third branch and the second branch and the third branch are next generation branches to the first branch.
7. The method of any one of examples 1-6, wherein the first positioning system comprises one or more position sensors.

8. The method of example 7, wherein the one or more position sensors comprises a fiber optic sensor.

9. The method of example 7, wherein the one or more position sensors comprises an electromagnetic sensor.

10. The method of any one of examples 7-9, wherein the flexible catheter includes the one or more position sensors to provide position and orientation of the distal portion of the flexible catheter.

11. The method of any one of examples 7-9, wherein the working catheter includes the one or more position sensors to provide position and orientation of the distal portion of the working catheter.

12. The method of any one of examples 1-11, wherein driving the distal portion of the flexible catheter to the first location further comprises:

receiving the working catheter within a lumen of the flexible catheter, wherein a distal end of the working catheter is positioned within the distal portion of the flexible catheter; and driving the working catheter to the first location while received within the lumen of the flexible catheter.

13. The method of any one of examples 1-3, 5-9, or 12, wherein a position and orientation of the flexible catheter is determined from the one or more position sensors in the working catheter.

14. The method of example 11, wherein driving the working catheter to the second location comprises using guidance from the one or more position sensors.

15. The method of example 7, wherein the imaging probe includes the one or more position sensors to provide position and orientation of the distal portion of the imaging probe.

16. The method of example 15, wherein driving the distal portion of the imaging probe to the third location comprises using guidance from the one or more position sensors.

17. The method of example 15, wherein driving the distal portion of the flexible catheter to the first location further comprises:

receiving the imaging probe within a lumen of the flexible catheter wherein a distal end of the imaging probe is positioned within the distal portion of the flexible catheter; and driving the imaging probe to the first location while received within a lumen of the flexible catheter.

18. The method of example 17, wherein a position and orientation of the flexible catheter is determined from the one or more position sensors in the imaging probe.

19. The method of any one of examples 1-6, further comprising using a second positioning system to guide the distal portion of the flexible catheter to the second location and to guide the distal portion of the imaging probe to the third location.

20. The method of example 19, wherein the second positioning system comprises:

a multi-port adaptor comprising a plurality of channels for receiving the working catheter, the imaging probe, and the flexible catheter; and an insertion measurement system for providing an imaging probe insertion position of the imaging probe and a flexible catheter insertion position of the flexible catheter.

21. The method of example 20, further comprising:

determining a working catheter position based on the first positioning system;

determining a relative radial position of the working catheter, the imaging probe, arid the flexible catheter based on known radial positions of the plurality of channels;

determining a position of the distal portion of the flexible catheter based on the relative radial position, the flexible catheter insertion position, and the working catheter position; and determining a position of the distal portion of the imaging probe based on the relative radial position, the imaging probe insertion position, and the working catheter position.

22. The method of any one of examples 1-21, wherein the flexible catheter further comprises one or more fiducials, and the imaging probe is configured to detect the one or more fiducials to localize the imaging probe to the flexible catheter.

23. The method of any one of examples 1-22, wherein the sealing device comprises one or more balloons.

24. The method of any one of examples 1-23, wherein collapsing the anatomic passageways distal to the sealing device further comprises removing air from the anatomic passageways using one or more first lumens in the working catheter, one or more second lumens in the imaging probe, or one or more third lumens in the flexible catheter.

25. The method of any one of examples 1-24, wherein the one or more medical instruments is selected from a group consisting of a biopsy needle, an ablation device, a cryotherapeutic device, a drug delivery needle, and an endoscope.

26. The method of any one of examples 1-25, wherein the anatomic passageways are airways of a lung and the target anatomy is a lesion or tumor.

27. The method of any one of examples 1-9 or 22-26, wherein:

the imaging probe is fixed to the flexible catheter;

the one or more imaging elements are positioned distal to the sealing device;

the sealing device is positioned at the first location; and the imaging elements are positioned at the third location.

28. The method of any one of examples 1-27, wherein the one or more imaging elements include at least one of a plurality of phased array ultrasound elements, a side facing ultrasound transducer, a forward facing ultrasound transducer, or a curved ultrasound transducer.

29. The method of any one of examples 1-27, wherein the imaging probe is a radial endo-bronchial probe.

30. The method of any one of examples 1-27, wherein the imaging probe includes an imaging needle configured to be inserted into target anatomy.

One or more elements in embodiments of the invention (e.g., method 900 and/or 800) may be implemented in software to execute on a processor of a computer system, such as control system 112. In some examples, the software may be included on non-transient, tangible, machine readable media that includes executable code that when run by one or more processors may cause the one or more processors to perform the processes of method 900 and/or 800. Some common forms of machine readable media that may include the processes of method 900 and/or 800 are, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read. In some examples, the software may be downloaded via computer networks such as the Internet, Intranet, etc. As described herein, operations of accessing, detecting, initiating, registered, displaying, receiving, generating, determining, moving data points, segmenting, matching, etc. may be performed at least in part by the control system 112 or the processors thereof.

Note that the processes and displays presented may not inherently be related to any particular computer or other apparatus. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A method for performing a minimally invasive procedure within anatomic passageways, comprising:
   activating a sealing device of a flexible catheter to seal the anatomic passageways at a sealing location, wherein the flexible catheter comprises a plurality of first lumens configured to receive a working catheter and an imaging probe including one or more imaging elements, wherein the one or more imaging elements comprise one or more ultrasound imaging elements;
   determining, with a positioning system, a position of at least one of a distal portion of the flexible catheter, a distal portion of the imaging probe, or a distal portion of the working catheter within the anatomic passageways while the imaging probe is positioned within a first of the plurality of first lumens, the working catheter is positioned within a second of the plurality of first lumens, and the imaging probe and the working catheter extend through the sealing device;
   collapsing a portion of the anatomic passageways distal of the sealing location by removing air from the anatomic passageways using at least one of a third of the plurality of first lumens, one or more second lumens in the working catheter, or one or more third lumens in the imaging probe; and
   capturing an image in the collapsed portion of the anatomic passageway using the one or more imaging elements of the imaging probe.

2. The method of claim 1, wherein activating the sealing device includes inflating one or more balloons of the sealing device.

3. The method of claim 2, wherein the one or more balloons are located at multiple points along the flexible catheter.

4. The method of claim 1, further comprising:
   removing, via one or more flaps or valves of the sealing device, air from the anatomic passageways as the portion of the anatomic passageways collapses.

5. The method of claim 1, wherein at least one of the flexible catheter, the imaging probe, or the working catheter includes one or more position sensors comprising at least one of a fiber optic sensor or an electromagnetic sensor.

6. The method of claim 1, further comprising:
   detecting, with the imaging probe, one or more fiducials of the flexible catheter or the working catheter.

7. The method of claim 1, wherein the one or more imaging elements of the imaging probe are positioned on an imaging needle of the imaging probe and capturing the image is performed while the imaging needle is disposed within a target anatomy.

8. The method of claim 1, wherein the one or more second lumens of the working catheter are configured to receive a medical instrument comprising a biopsy needle, an ablation device, a cryotherapeutic device, a drug delivery needle, or an endoscope.

9. The method of claim 1, wherein the one or more ultrasound imaging elements include at least one of a plurality of phased array ultrasound elements, a side facing ultrasound transducer, a forward facing ultrasound transducer, or a curved ultrasound transducer.

10. A method for performing a minimally invasive procedure within anatomic passageways, comprising:
    receiving a working catheter, an imaging probe, and a flexible catheter in a multi-port adaptor comprising a plurality of channels;
    activating a sealing device of the flexible catheter to seal the anatomic passageways at a sealing location;
    collapsing the anatomic passageways distal of the sealing location by removing air from the anatomic passageways while the imaging probe and the working catheter extend through the sealing device, the imaging probe comprising one or more imaging elements positioned near a distal portion of the imaging probe and configured to obtain images of a target anatomy, the working catheter comprising one or more first lumens configured to receive a medical instrument; and
    determining, with a positioning system, at least one of a position of a distal portion of the working catheter, a position of the distal portion of the imaging probe, or a position of a distal portion of the flexible catheter within the anatomic passageways, wherein the positioning system includes at least one position sensor comprising at least one of a fiber optic sensor or an electromagnetic sensor wherein the at least one position sensor includes a first position sensor fixedly coupled to the working catheter.

11. The method of claim 10, further comprising:
    removing air from the anatomic passageways with one or more flaps or valves of the sealing device as the anatomic passageways distal of the sealing location collapse.

12. The method of claim 10, wherein the sealing device comprises balloons located at multiple points along the flexible catheter.

13. A method for performing a minimally invasive procedure within anatomic passageways, comprising:
    activating a sealing device of a flexible catheter to seal the anatomic passageways at a sealing location;
    collapsing the anatomic passageways distal of the sealing location by removing air from the anatomic passageways while an imaging probe and a working catheter extend through the sealing device, the imaging probe comprising one or more imaging elements positioned near a distal portion of the imaging probe and configured to obtain images of a target anatomy, the working catheter comprising one or more first lumens configured to receive a medical instrument;
    capturing an image of the target anatomy when the distal portion of the imaging probe is positioned within a first branch of the anatomic passageways and a distal portion of the working catheter is positioned within a second branch of the anatomic passageways, wherein the target anatomy is within tissue between the first branch and the second branch; and determining, with a positioning system, at least one of a position of the distal portion of the working catheter, a position of the distal portion of the imaging probe, or a position of a distal portion of the flexible catheter within the anatomic passageways.

14. The method of claim 10, further comprising:

providing, with an insertion measurement system, an imaging probe insertion position of the imaging probe or a flexible catheter insertion position of the flexible catheter;

determining a relative position of the working catheter, the imaging probe, or the flexible catheter based on a known configuration of the plurality of channels;

determining the position of the distal portion of the working catheter based on data from the at least one position sensor; and determining the position of the distal portion of the imaging probe based on the relative position, the position of the distal portion of the working catheter, the imaging probe insertion position, and the images of the target anatomy.

15. The method of claim 10, wherein the at least one position sensor includes a second position sensor received within one or more second lumens of the imaging probe.

16. The method of claim 10, further comprising:

detecting, with the imaging probe, one or more fiducials of the working catheter.

* * * * *